US012606609B2

(12) United States Patent  
Curstedt et al.

(10) Patent No.: US 12,606,609 B2  
(45) Date of Patent: Apr. 21, 2026

(54) POLYPEPTIDES HAVING IMPROVED PROPERTIES

(71) Applicant: CHIESI FARMACEUTICI S.p.A., Parma (IT)

(72) Inventors: Tore Curstedt, Parma (IT); Jan Johansson, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 825 days.

(21) Appl. No.: 17/759,613

(22) PCT Filed: Jan. 26, 2021

(86) PCT No.: PCT/EP2021/051665

§ 371 (c)(1),  
(2) Date: Jul. 27, 2022

(87) PCT Pub. No.: WO2021/151853

PCT Pub. Date: Aug. 5, 2021

(65) Prior Publication Data

US 2023/0257446 A1     Aug. 17, 2023

(30) Foreign Application Priority Data

Jan. 28, 2020    (EP) .................................... 20153979

(51) Int. Cl.

| | |
|---|---|
| *C07K 14/785* | (2006.01) |
| *A61K 38/16* | (2006.01) |
| *A61K 47/24* | (2006.01) |
| *A61P 11/00* | (2006.01) |

(52) U.S. Cl.

CPC ............ *C07K 14/785* (2013.01); *A61K 38/16* (2013.01); *A61K 47/24* (2013.01); *A61P 11/00* (2018.01); *C07K 2319/21* (2013.01)

(58) Field of Classification Search

CPC ... C07K 14/785; C07K 2319/21; A61P 11/00; A61K 38/16; A61K 47/24

See application file for complete search history.

(56) References Cited

U.S. PATENT DOCUMENTS

| | | | |
|---|---|---|---|
| 6,660,833 B1 | 12/2003 | Walther et al. | |
| 2013/0303726 A1 | 11/2013 | Mozzarelli et al. | |
| 2018/0055914 A1* | 3/2018 | Sartor ...................... | A61K 9/06 |

FOREIGN PATENT DOCUMENTS

| | | | |
|---|---|---|---|
| EP | 413957 | A2 | 2/1991 |
| WO | WO-8906657 | A1 | 7/1989 |
| WO | WO-9118015 | A1 | 11/1991 |
| WO | WO-9222315 | A1 | 12/1992 |
| WO | WO-9532992 | A1 | 12/1995 |
| WO | WO-9849191 | A1 | 11/1998 |
| WO | WO-0047623 | A1 | 8/2000 |
| WO | WO-2004105726 | A1 | 12/2004 |
| WO | WO-2005073246 | A2 | 8/2005 |
| WO | WO-2008011559 | A2 | 1/2008 |
| WO | WO-2008044109 | A1 | 4/2008 |
| WO | WO-2008148469 | A1 | 12/2008 |
| WO | WO-2010139442 | A1 | 12/2010 |
| WO | WO-2013120058 | A2 | 8/2013 |
| WO | WO-2014079898 | A1 | 5/2014 |
| WO | WO-2017081239 | A1 | 5/2017 |
| WO | WO-2017106742 | A1 | 6/2017 |

OTHER PUBLICATIONS

Das et al, Codrug: An efficient approach for drug optimization, European Journal of Pharmaceutical Sciences, 2010, 41, pp. 571-588.*

Almlen, A., et al., "Synthetic surfactant based on analogues of SP-B and SP-C is superior to single-peptide surfactants in ventilated premature rabbits," Neonatology 98(1):91-99, IOP Publishing, United Kingdom (2010).

Dargaville, P.A., et al., "Minimally-invasive surfactant therapy in preterm infants on continuous positive airway pressure," *Arch. Dis. Fetal. Neonatal. Ed.* 98(2):122-126, BMJ, United Kingdom (2013).

Esposito, D., and Chatterjee, D.K., "Enhancement of soluble protein expression through the use of fusion tags," *Curr. Opin. Biotechnol.* 17:353-358, Elsevier, Netherlands (2006).

Ferrer-Miralles, N., et al., "General introduction: recombinant protein production and purification of insoluble proteins," *Methods. Mol. Biol.* 1258:1-24, Humana Press, United States (2015).

Liu, X., et al., "The expression of pulmonary surfactant proteins B and surfactant protein C in *E. coli*," *Zhonghua Yi Xue Za Zhi* 76(6):447-450, Taipei, Taiwan (Jun. 1996), only those in English.

Meienhofer, J., "3-Peptide Synthesis: A Review of the Solid-Phase Method," in *Hormonal Proteins and Peptides*, vol. 2, Li, C.H., ed., p. 46, Academic Press, United States (1983).

(Continued)

*Primary Examiner* — Li N Komatsu

(74) *Attorney, Agent, or Firm* — Element IP, PLC

(57) ABSTRACT

The present invention is directed to polypeptides having the properties of both SP-C and SP-B surfactant proteins and to the corresponding reconstituted surfactants. The invention is also directed to the pharmaceutical compositions thereof and to their use for the treatment or prophylaxis of neonatal respiratory distress syndrome (RDS) or other respiratory disorders such as acute RDS.

30 Claims, 4 Drawing Sheets

Figure 1A:
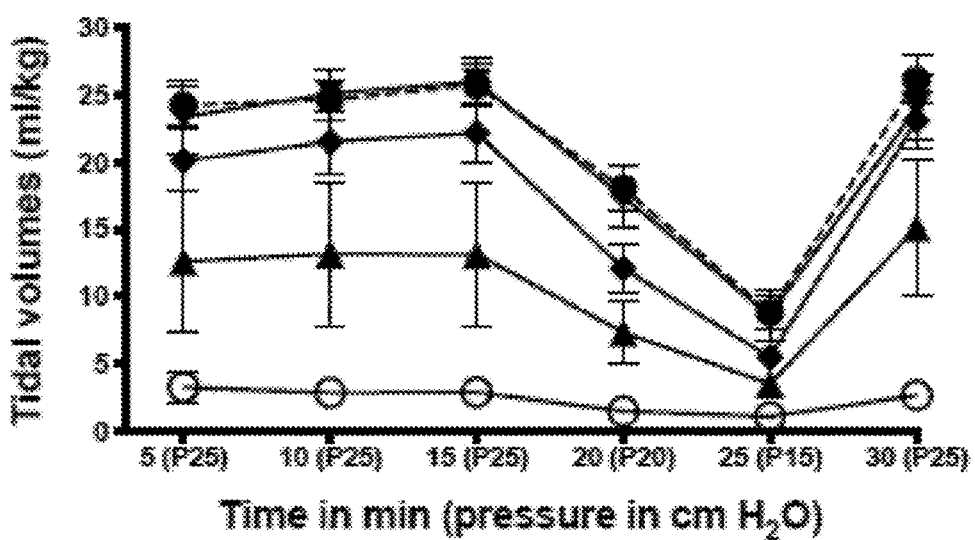

Specification includes a Sequence Listing.

(56) References Cited

OTHER PUBLICATIONS

Merrifield, R.B., et al., "Solid Phase Peptide Synthesis. I. The Synthesis of a Tetrapeptide," *J. Am. Chem. Soc.* 85:2149-2154, American Chemical Society, United States (1963).

Scherle, W., "A simple method for volumetry of organs in quantitative stereology," *Mikroskopie* 26:57-60, Wiley, United States (1970).

Walther, F.J., et al., "Synthetic surfactant containing SP-B and SP-C mimics is superior to single-peptide formulations in rabbits with chemical acute lung injury," *PeerJ* 2:e393, O'Reilly, United States (2014).

* cited by examiner

POLYPEPTIDES HAVING IMPROVED PROPERTIES

The content of the electronically submitted sequence listing in ASCII text file (Name: 4559_0370001_Seg-listing_ST25; Size: 29,944 bytes; and Date of Creation: Jul. 12, 2022) filed with the application is incorporated herein by reference in its entirety.

FIELD OF THE INVENTION

The present invention is directed to polypeptides having the properties of both SP-C and SP-B surfactant proteins. Said polypeptides shall be used for the preparation of reconstituted surfactants comprising a lipid carrier.

The invention is also directed to the pharmaceutical compositions thereof and to their use for the treatment or prophylaxis of neonatal respiratory distress syndrome (RDS) and other respiratory disorders such as acute RDS.

BACKGROUND OF THE INVENTION

The human lung is composed of many small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

Lung surfactant complex is primarily composed of lipids and contains minor amounts of various proteins. An absence of adequate levels of this complex results in malfunction of the lungs.

This syndrome is called Respiratory Distress Syndrome (RDS) and it commonly affects preterm infants.

Said syndrome is effectively treated with modified natural surfactant preparations extracted from animal lungs.

Commercially available modified natural surfactant preparations are, for example, Curosurf™ (Chiesi Farmaceutici SpA, Parma, Italy), derived from porcine lung, Infasurf™ (Forest Pharmaceuticals, St. Louis, Missouri) extracted form calf lung lavage and Survanta™ (Abbvie Inc, North Chicago, Illinois) a chemically modified natural bovine lung extract.

The main constituents of these surfactant preparations are phospholipids such as 1,2-dipalmitoyl-sn-glycero-3-phos-phocholine, commonly known as dipalmitoyl-phosphatidyl-choline (DPPC), and phosphatidylglycerol (PG), and surfactant hydrophobic proteins B and C (SP B and SP C).

Modified natural surfactants could also be used for the treatment of an acute RDS form affecting the pediatric and adult populations and known as ARDS, whose causes are direct or indirect lung injuries.

Due to the drawbacks of the surfactant preparations from animal tissues, such as the complication of the production and sterilization processes and possible induction of immune reactions, synthetic surfactants mimicking the composition of the modified natural surfactants have been developed.

Said synthetic surfactants are also known as reconstituted surfactants. However, the development of clinically active reconstituted surfactants has turned out to be complicated since the native hydrophobic proteins are too big to synthesize, structurally complex and are unstable in pure form.

To replace said native hydrophobic proteins, some synthetic polypeptides, partially corresponding to their sequences and analogs thereof have been proposed in the prior art, and are for example disclosed in WO 89/06657, WO 92/22315, WO 98/49191, WO 95/32992, U.S. Pat. No.

6,660,833, EP 413,957 and WO 91/18015, WO 00/47623, and WO 2008/011559, and WO 2013/120058.

On the other hand, it has recently been established that in order to achieve an efficacy in terms of lung compliance comparable to that of the surfactants extracted from animals, reconstituted surfactants should have a composition reproducing the complete proteinaceous profile of the modified natural surfactants.

For example, this has been highlighted in WO 2008/044109, WO 2010/139442, and by Vovan et al (Abstracts of the 2006 Pediatric Academy Society Annual Meeting, April 29-May 2 San Francisco, California) and Amlen A et al (Neonatology. 2010 June; 98(1):91-9) wherein reconstituted surfactants comprising both an analogue of SP-C and an analogue of SP-B have been disclosed and tested.

However, there is still an unmet need for reconstituted surfactants simpler and more cost-efficient to prepare, wherein the polypeptides combine the properties of both SP-B and SP-C proteins into a single polypeptidic chain.

It has now been found, and it is the object of the present invention, that unique peptides having the properties of both SP-C and SP-B proteins could be designed in order to provide reconstituted surfactant preparations with excellent properties in terms of lung compliance.

In particular, it has been found that, in an animal model of RDS, an exogenous surfactant preparation comprising one the polypeptides of the invention efficaciously act on both tidal volumes, lung compliance volumes and lung gas volumes.

SUMMARY OF THE INVENTION

The present invention is directed to a polypeptide having a sequence represented by the following general formula (I):

$$F_qP_qI_qP_qL_qP_qY_qLWL\Phi ZALIZZIQA\Omega IPZGGZ\Omega LPQLV\Phi ZLVLZLS(GS)_nG_rI$$
$$PSSPVHLZZXBXXXXXXXXXXXXXXXXGALL\Omega_pG_pL_p$$
$$(SEQ\ ID\ NO:\ 7) \qquad (I)$$

wherein:

Ω is an amino acid residue independently selected from the group consisting of M, or M oxidized on the sulfur atom, I, L and Nle;

Φ is an amino acid residue independently selected from the group consisting of L, I, and C, preferably L;

X is an amino acid residue independently selected from the group consisting of I, L, and Nle, preferably I or L;

B is an amino acid residue independently selected from the group consisting of K, R, H, W, F, Y, and Orn;

Z is an amino acid selected from K or R p and q are integers having a value of 0 or 1;

n is an integer having a value comprised between 1 and 8, preferably comprised between 1 and 4; and r is an integer having a value of 0 or 1.

The polypeptides of the invention also encompass the pharmaceutically acceptable salts of said polypeptides and their blocked N- and/or C-terminus derivatives, e.g via acylation and amidation.

The side-chains of the polypeptides might also be acylated.

In a second aspect, the invention is directed to a synthetic or recombinant process for the preparation of the polypeptides of the invention.

In a third aspect, the invention is directed to a medicament in form of a reconstituted surfactant comprising one or more polypeptides of general formula (I) in combination with a lipid carrier.

In a fourth aspect, the invention is directed to a pharmaceutical formulation comprising a reconstituted surfactant according to the invention alone or in combination with one or more pharmaceutically acceptable carriers.

In a fifth aspect, the invention refers to the polypeptides of the invention for use as a medicament.

In a sixth aspect, the invention is directed to the polypeptides of general formula (I) for use for the prophylaxis and/or treatment of a disease related to the lack and/or dysfunction of the endogenous pulmonary surfactant such as neonatal or acute respiratory distress syndrome (RDS).

In a seventh aspect, the invention provides the use of the polypeptides of general formula (I) for the manufacture of a medicament for the prophylaxis and/or treatment of a disease related to the lack and/or dysfunction of the endogenous pulmonary surfactant such as neonatal or acute respiratory distress syndrome (RDS).

In an eighth aspect, the invention provides a method for the prophylaxis and/or treatment of a disease related to the lack and/or dysfunction of the endogenous pulmonary surfactant, said method comprising administering to a patient in need of such treatment a therapeutically effective amount of one or more polypeptides of general formula (I).

In a ninth aspect, the invention is directed to a kit, comprising: a) the reconstituted surfactant according to the invention in a powder form in a first unit dosage form; b) a pharmaceutically acceptable carrier in a second unit dosage form; and c) container means for containing said first and second dosage forms.

In a tenth, aspect, the invention is directed to a nucleic acid sequence encoding for the claimed polypeptides.

FIGURES

Figure 1B:
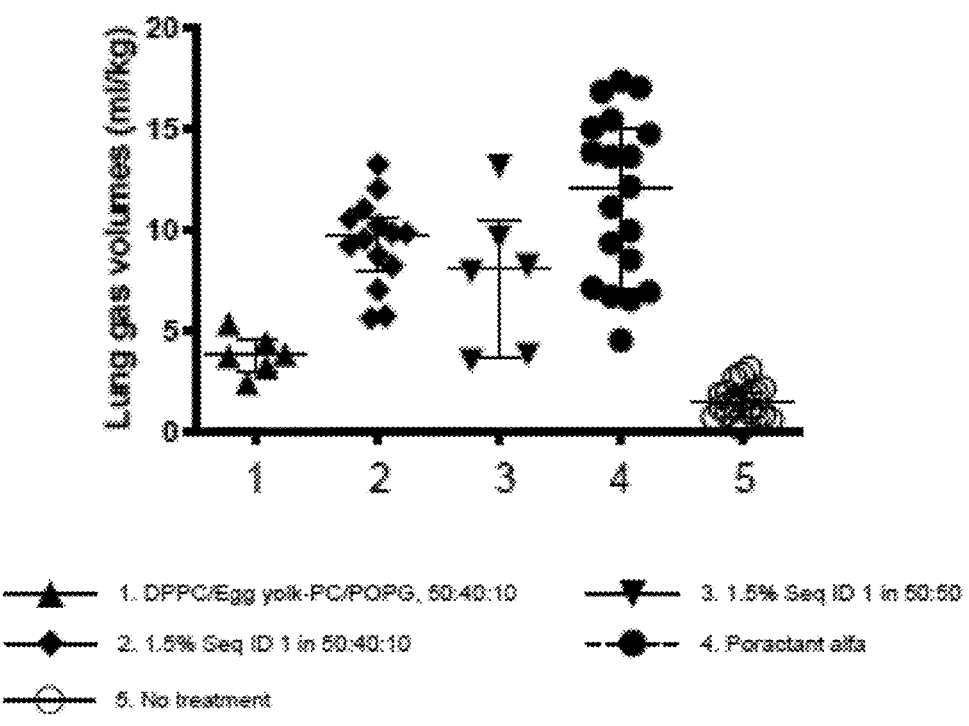

FIGS. 1A and 1B. Activity of surfactants comprising combo peptides in a rabbit model of neonatal RDS. Line graphs (FIG. 1A) show tidal volume means±SE during the 30 min ventilation period, dot plots (FIG. 1B) present the lung gas volumes median and interquartile ranges after 30 min of ventilation. Animals were untreated, treated with SEQ ID NO:1 in DPPC/egg yolk-PC/POPG 50:40:10, or in DPPC/POPG 50:50, or poractant alfa, or phospholipids only, as indicated under the graphs. **=p≤0.01.

Figure 2A:
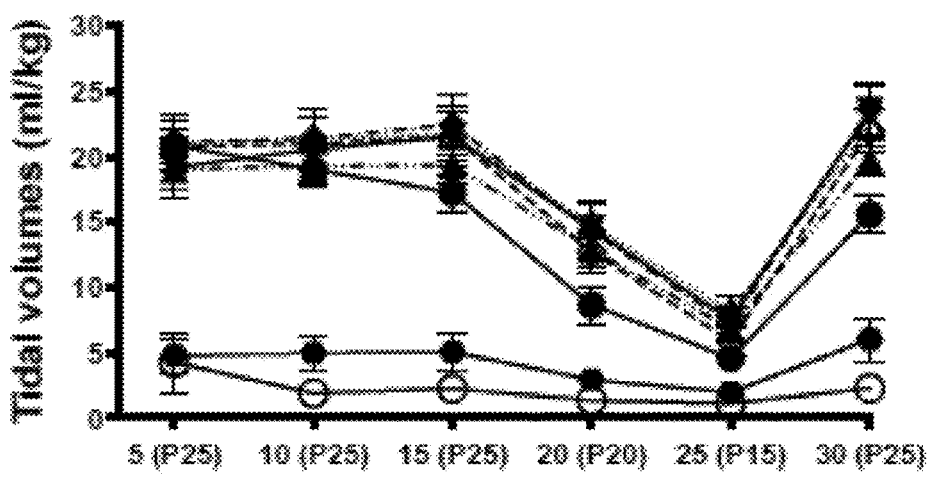
Figure 2B:
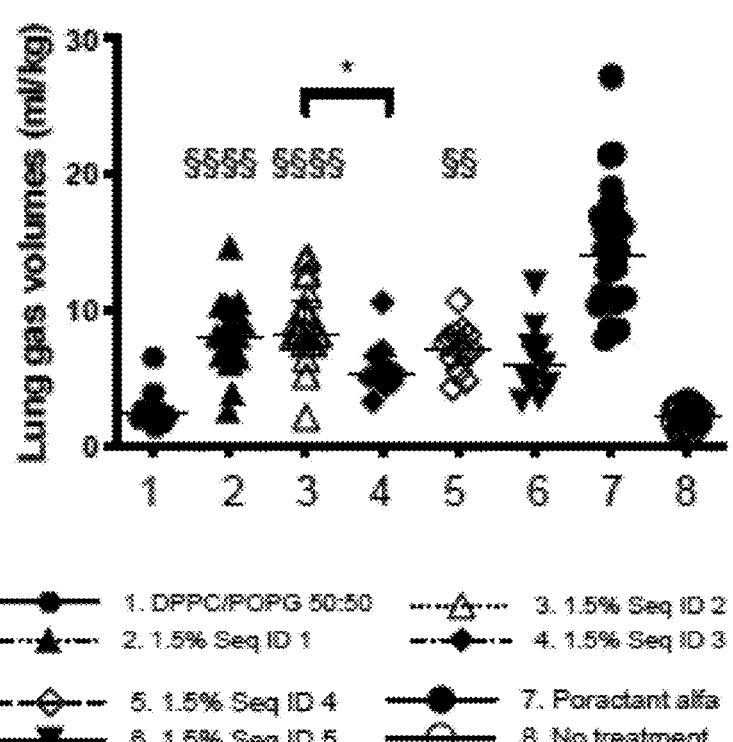

FIGS. 2A and 2B. Activities of synthetic surfactants containing 1.5% of SEQ ID NOS:1-5 in a rabbit model of neonatal RDS. Line graphs (FIG. 2A) show tidal volume means±SE during the 30 min ventilation period, dot plots (FIG. 2B) present the lung gas volumes median and interquartile ranges after 30 min of ventilation. Animals were untreated, treated with 1.5% (w/w) of SEQ ID NOS:1-5, respectively, in DPPC/POPG 50:50, or poractant alfa, or phospholipids only, as indicated under the graphs. *=p≤0.1. § § =p≤0.01 and § §§ § =p≤0.0001 versus phospholipids DPPC/POPG 50:50 only.

Figure 3A:
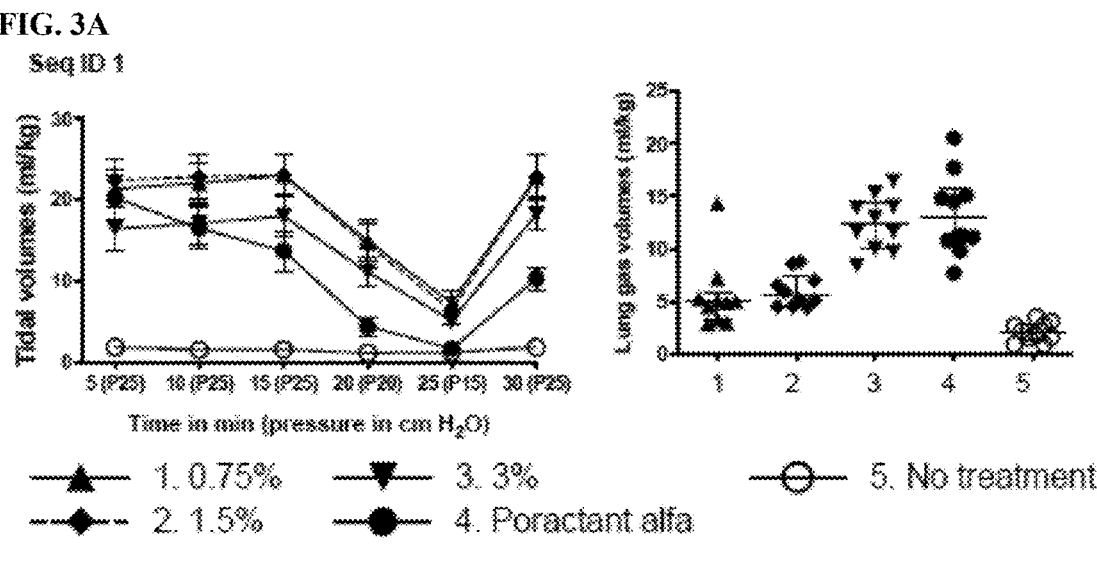
Figure 3B:
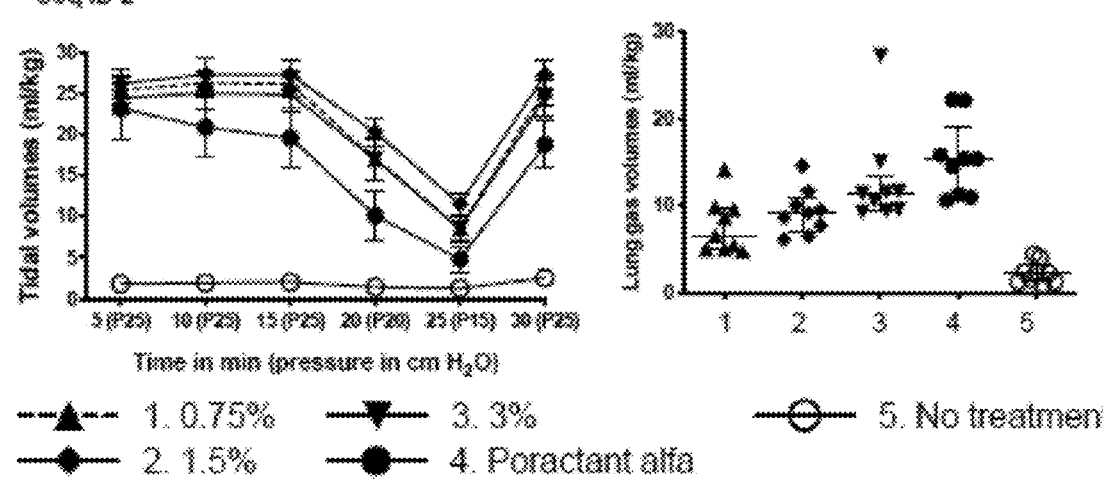
Figure 3C:
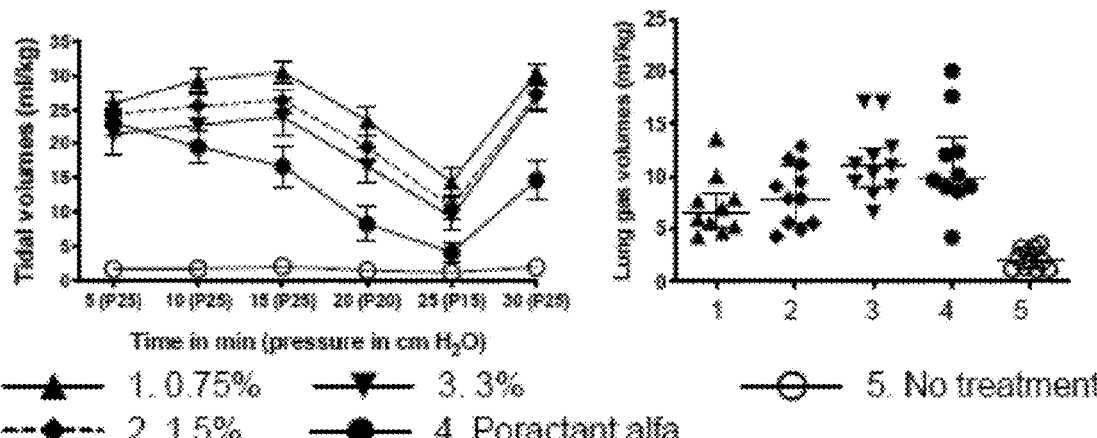

FIGS. 3A, 3B, and 3C. Combo peptide concentration effects on efficacy in a rabbit model of neonatal RDS. Line graphs (left sides of FIGS. 3A, 3B, and 3C) show tidal volume means±SE during the 30 min ventilation period, dot plots (right sides of FIGS. 3A, 3B, and 3C) present the lung gas volumes median and interquartile ranges after 30 min of ventilation. Animals were untreated, treated with 0.75%, 1.5% or 3% (w/w) of SEQ ID NOS:1-3, respectively in DPPC/POPG 50:50, or poractant alfa, as indicated under the graphs.

Figure 4A:
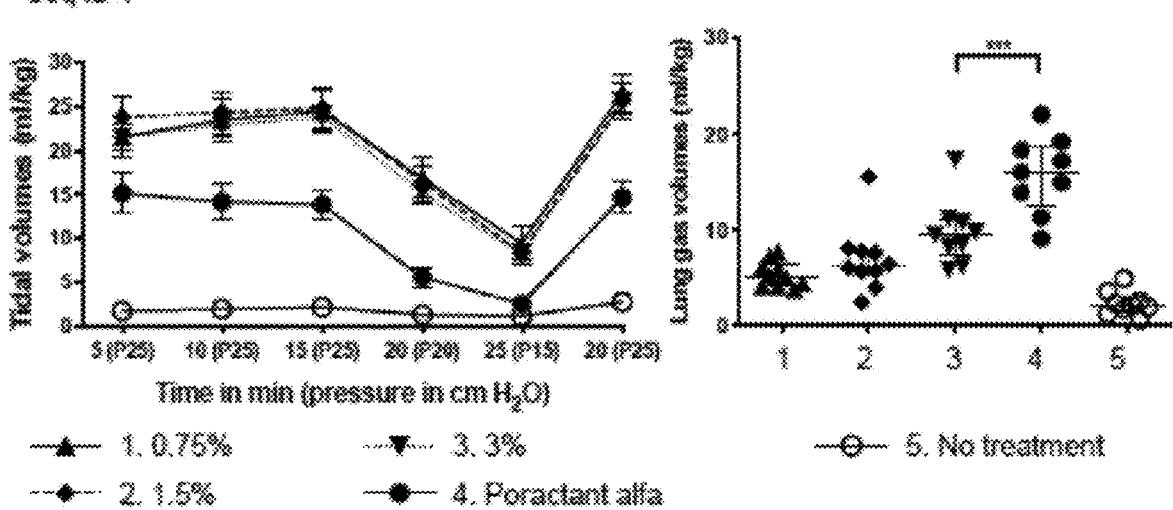
Figure 4B:
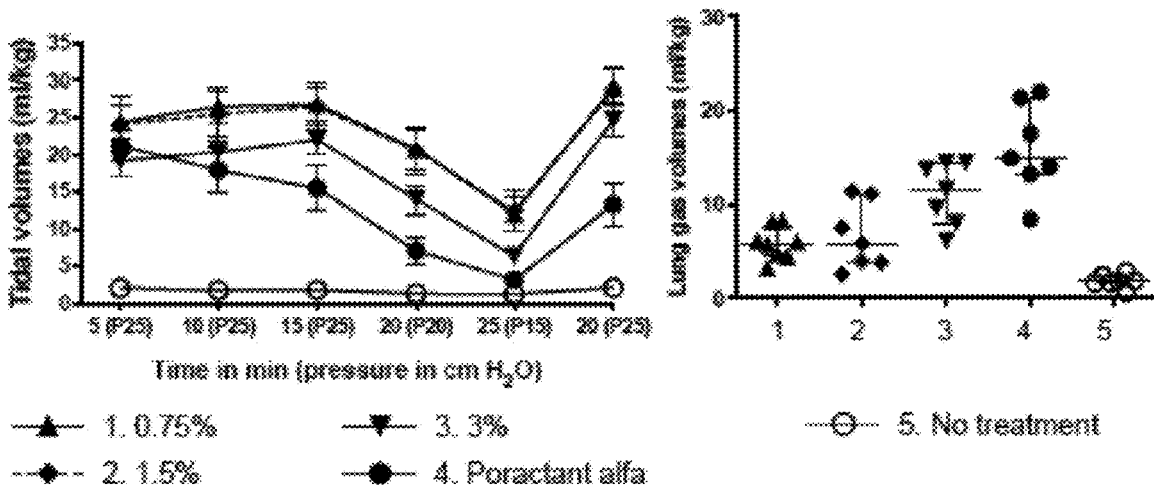

FIGS. 4A and 4B. Combo peptide concentration effects on efficacy in a rabbit model of neonatal RDS. Line graphs (left sides of FIGS. 4A and 4B) show tidal volume means±SE during the 30 min ventilation period, dot plots (right sides of FIGS. 4A and 4B) present the lung gas volumes median and interquartile ranges after 30 min of ventilation. Animals were untreated, treated with 0.75%, 1.5% or 3% (w/w) of SEQ ID NOS: 4-5 in DPPC/POPG 50:50, or poractant alfa, as indicated under the graphs. ***=p<0.001.

DEFINITIONS

The terms "neonates", "newborns" and "infants" are used interchangeably.

The respiratory function after in vivo treatment with the exogenous surfactant preparations is carried out by measuring two parameters:

i) the tidal volume which is an index of the lung compliance and ii) the lung gas volume which is an index of the alveolar air expansion or patency at the end of expiration, and hence of the capability of forming a stable phospholipidic film in the alveoli at the end of expiration.

The term "reconstituted surfactant" means a lipid carrier to which polypeptide analogues of the surfactant proteins, made through recombinant technology or synthetic methods, have been added. In the context of the present application, the terms "synthetic" and "reconstituted" are used as synonymous.

The term "lipid carrier" means a mixture of phospholipids and optionally further lipid components, for example neutral lipids such as triacylglycerols, free fatty acids and/or cholesterol.

The term "variants" means analogues of the polypeptides of general formula (i) having an amino acid sequence in which one or more amino acids have been replaced by other amino acids, so long as the polypeptides, in a mixture with a lipid carrier, retain the same activity.

The term "pre-term neonate", or premature neonate, includes extremely low birth weight (ELBW), very-low-birth-weight (VLBW), and low-birth weight (LBW) neonates of 24-35 weeks gestational age.

The term "non-invasive ventilation (NIV) procedure" defines a ventilation modality that supports breathing without the need for intubation such as nasal Continuous Positive Airway Pressure (nasal CPAP). Other non-invasive ventilation procedures are nasal intermittent positive-pressure ventilation (NIPPV), High Flow Nasal Cannula (HFNC), and bi-level positive airway pressure (BiPAP).

The term "respiratory support" includes any intervention that treats respiratory illness including, for example, the administration of supplemental oxygen, mechanical ventilation, and nasal CPAP.

The term "therapeutically effective amount" means the amount of the active ingredient, that, when delivered to neonates, provides the desired biological effect.

The term "prevention" refers to the therapeutic use for progression-slowing and/or onset delaying of the disease.

The term "treatment" refers to the therapeutic use for palliative, curing, symptom-allievating, symptom-reducing, disease regression-inducing therapy.

The term "phospholipids" refers to a class of lipids constituted of glycerol, a phosphate group, a neutral or zwitter-ionic moiety as the characterizing part; one exception to this rule is sphingomyelin, which is derived from sphingosine instead of glycerol. The glycerol moiety or the sphingosine residue can be esterified with long chain fatty acids ($C_{14}$-$C_{22}$) which in turn can be saturated (e.g. myristic, palmitic and stearic acid), monounsaturated (e.g. oleic acid) or polyunsaturated (e.g. linoleic and arachidonic acid).

The amino acid sequences are shown according to the one-letter code with the amino acid which carries the free amino group at the left end (amino terminus) and the amino acid which carries the free carboxyl group at the right end (carboxy terminus).

All the amino acid residues identified herein are in the natural L-configuration and the sequences identified herein are reported according to standard abbreviations for amino acid residues as shown in the following Table of Correspondence.

TABLE OF CORRESPONDENCE

| AMINO ACID | SYMBOL | |
| | One letter | Three letter |
| --- | --- | --- |
| Glycine | G | Gly |
| L-proline | PP | Pro |
| L-isoleucine | I | Ile |
| L-leucine | L | Leu |
| L-tyrosine | Y | Tyr |
| L-cysteine | C | Cys |
| L-tryptophane | W | Trp |
| L-alanine | A | Ala |
| L-lysine | K | Lys |
| L-arginine | R | Arg |
| L-glutamine | Q | Glu |
| L-methionine | M | Met |
| L-serine | S | Ser |
| L-valine | V | Val |
| L-aspargine | N | Asn |
| L-aspartic acid | D | Asp |
| L-glutamic acid | E | Gln |
| L-histidine | H | His |
| L-threonine | T | Thr |
| L-phenylalanine | F | Phe |
| L-nor-leucine | Nle | nLeu |
| L-ornithine | — | Orn |

DETAILED DESCRIPTION OF THE INVENTION

The present invention is directed to polypeptides having in a unique sequence the properties of both SP-C and SP-B surfactant proteins (hereinafter combo peptides).

Said polypeptides are used for the preparation of a reconstituted surfactant comprising a lipid carrier.

We have found that, in a model of RDS wherein the immature rabbit newborns are treated without applying external positive end-expiratory pressure (PEEP), an exogenous surfactant preparation comprising one the polypeptides of general formula (I) efficaciously act on both tidal volumes, lung compliance volumes and lung gas volumes.

The efficacy without the use of an external source of ventilation is rather surprising, and make the peptides of the invention virtually useful for treating newborns kept under non-invasive ventilation procedures as well.

Furthermore, the results demonstrate that reconstituted surfactants comprising the polypeptides of the invention can stabilize the phospholipid film in the alveoli at the end of expiration in the same way as a reconstituted surfactant comprising both an analogue of the protein SP-C or an analogue of the protein SP-B.

Moreover, the reconstituted surfactants made from the combo peptides of the invention turned out to be similairly active as one of the most used modified natural surfactant for RDS, with the advantage that can be produced in a simpler and more cost-efficient manner.

Further, the combo peptides of the invention turned to be efficacious at rather low doses, i.e. 0.1-3%. This could be advantage as it is well known that at higher concentrations of the peptides, the viscosity of the reconstituted surfactant preparations tends to increase.

The use of only a unique peptide combining the properties of both SP-C and SP-B proteins might also make easier to control the viscosity of the formulalation than adding two different peptides, each one with different viscosity properties.

Advantageously, the polypeptides have a sequence represented by the following general formula (I):

(SEQ ID NO: 7)
$F_qP_qI_qP_qL_qP_qY_q$LWL$\Phi$ZALIZZIQA$\Omega$IPZGGZ$\Omega$LPQLV$\Phi$ZLVLZLS
(GS)$_n$G$_r$IPSSPVHLZZXBXXXXXXXXXXXXXXXXGALL$\Omega_p$G$_p$L$_p$ (I), wherein:

$\Omega$ is an amino acid residue independently selected from the group consisting of M, or M oxidized on the sulfur atom, I, L and Nle;

$\Phi$ is an amino acid residue independently selected from the group consisting of L, I, and C, preferably L;

X is an amino acid residue independently selected from the group consisting of I, L, and Nle, preferably I or L;

B is an amino acid residue independently selected from the group consisting of K, R, H, W, F, Y, and Orn;

Z is an amino acid selected from K or R p and q are integers having a value of 0 or 1;

n is an integer having a value comprised between 1 and 8, preferably comprised between 1 and 4; and r is an integer having a value of 0 or 1.

In a particular embodiment, when $\Phi$ is C, the polypeptides may form intramolecular disulfide linkages between said cysteine residues.

Preferably, the integer p is 1.

In one of the preferred embodiments, the polypeptides of the invention could have the general formula (II)

It was indeed found that analogues of the SP-B protein comprising the N-terminal part sequence FPIPLPY increases oxygenation and compliance in animal models of acute RDS (ARDS), and hence they could be suitable for the treatment of RDS in the pediatric and adult populations (see Walther F J et al PeerJ 2014, 2, e393).

(SEQ ID NO: 8)
FPIPLPYLWL$\Phi$ZALIZZIQA$\Omega$IPZGGZ$\Omega$LPQLV$\Phi$ZLVLZLS(GS)$_n$G$_r$I
PSSPVHLZZXBXXXXXXXXXXXXXXXXGALL$\Omega_p$G$_p$L$_p$ (II)

Wherein p is 0 or 1, preferably 1;

r is 0 or 1;

n is 1 to 4; and $\Phi$, X, B, $\Omega$ and Z are as defined above.

Accordingly, a first group of preferred polypeptides of the invention has the general formula (IIa):

(SEQ ID NO: 9)
FPIPLPYLWL$\Phi$RALIKRIQA$\Omega$IPKGGR$\Omega$LPQLV$\Phi$RLVLRLSGSGSGSGS
IPSSPVHLKRXBXXXXXXXXXXXXXXXXGALL$\Omega$GL (IIa)

wherein $\Phi$, X, B and $\Omega$ are as defined above.

A second group of preferred polypeptides of the invention has the general formula (IIb):

```
                                    (SEQ ID NO: 10)
FPIPLPYLWLΦRALIKRIQAΩIPKGGRΩLPQLVΦRLVLRLSGSGIPSSP
VHLKRXBXXXXXXXXXXXXXXXXGALLΩGL (IIb)
``` wherein Φ, X, B and Ω are as defined above.

A third group of preferred polypeptides of the invention has the general formula (IIc):

```
                                    (SEQ ID NO: 11)
FPIPLPYLWLΦRALIKRIQAQIPKGGRΩLPQLVΦRLVLRLSGSGSGSGS
IPSSPVHLKRXBXXXXXXXXXXXXXXXGALL (IIc)
``` wherein Φ, X, B and Ω are as defined above.

A fourth group of preferred polypeptides of the invention has the general formula (IId):

```
                                    (SEQ ID NO: 12)
FPIPLPYLWLΦRALIKRIQAΩIPKGGRΩLPQLVΦRLVLRLSGSGIPSSP
VHLKRXBXXXXXXXXXXXXXXXGALL (IId)
``` wherein Φ, X, B and Ω are as defined above.

Yet, in another one of the preferred embodiments, the polypeptides of the invention could have the general formula (III)

```
                                    (SEQ ID NO: 13)
LWLΦRALIKRIQΩAIPKGGRΩLPQLVΦRLVLRLS(GS)ₙG,IPSSPVHL
KRXBXXXXXXXXXXXXXXXXGALLΩpGpLp (III)
```

Wherein p is 0 or 1, preferably 1;

r is 0 or 1;

n is 1 to 4; and

Φ, X, B, Ω and Z are as defined above.

Said shorter polypeptides would particularly be advantageous for the prevention and/or treatment of any disease associated to the lack and/or dysfunction of the endogenous pulmonary surfactant which may benefit of an improved resistance to inactivation.

Accordingly, a fifth group of preferred polypeptides of the invention as the general formula (IIIe):

```
                                    (SEQ ID NO: 14)
LWLΦRALIKRIQAΩIPKGGRΩLPQLVΦRLVLRLSGSGSGSGSIPSSPVH
LKRXBXXXXXXXXXXXXXXXXGALLΩGL (IIIe)
``` wherein Φ, X, B and Ω are as defined above.

A sixth group of preferred polypeptides of the invention has the general formula (IIIf):

```
                                    (SEQ ID NO: 15)
LWLΦRALIKRIQAΩIPKGGRΩLPQLVΦRLVLRLSGSGIPSSPVHLKRXB
XXXXXXXXXXXXXXXGALLΩGL (IIIf)
``` wherein Φ, X, B and Ω are as defined above.

A seventh group of preferred polypeptides of the invention has the general formula (IIIg):

```
                                    (SEQ ID NO: 16)
LWLΦRALIKRIQAΩIPKGGRΩLPQLVΦRLVLRLSGSGSGSGSIPSSPVH
LKRXBXXXXXXXXXXXXXXXXGALL (IIIg)
``` wherein Φ, X, B and Ω are as defined above.

An eighth group of preferred polypeptides of the invention has the general formula (IIIh):

```
                                    (SEQ ID NO: 17)
LWLΦRALIKRIQAΩIPKGGRΩLPQLVΦRLVLRLSGSGIPSSPVHLKRXB
XXXXXXXXXXXXXXXXGALL (IIIh)
``` wherein Φ, X, B and Ω are as defined above.

Particularly preferred are the polypeptides wherein the sequence

```
            (residues 56-69 of SEQ ID NO: 18)
     XXXXXXXXXXXXXX is LLLLLLLLILLLLIL
```

In has indeed been found that said sequence turned to be very useful in promoting alpha-helix formation, while avoiding the formation of insoluble beta-sheet aggregates and amyloid-like fibrils.

Accordingly, more preferred groups of polypeptides of the invention have the following general formula (IV):

```
                                    (SEQ ID NO: 18)
FqPqIqPqLqPqYqLWLΦRALIKRIQAΩIPKGGRΩLPQLVΦRLVLRLS
(GS)ₙG,IPSSPVHLKRXBLLLLLLLLLILLLILGALLΩGL (IV)
```

Wherein q is 0 or 1;

r is 0 or 1;

n is 1 to 4; and

Φ, B and Ω are as defined above.

In a particular subgroup of general formula (IV), said polypeptides have the following general formula (IVi):

```
                                    (SEQ ID NO: 19)
FPIPLPYLWLΦRALIKRIQAΩIPKGGRΩLPQLVΦRLVLRLS(GS)ₙG,I
PSSPVHLKRXBLLLLLLLLLILLLILGALLΩGL (IVi)
```

Wherein r is 0 or 1;

n is 1 to 4; and

Φ, B and Ω are as defined above.

In another subgroup, said polypeptides have the following general formula (IVI):

```
                                    (SEQ ID NO: 20)
LWLΦRALIKRIQAΩIPKGGRΩLPQLVΦRLVLRLS(GS)ₙG,IPSSPVHL
KRXBLLLLLLLLLILLLILGALLΩGL (IVI)
```

Wherein r is 0 or 1;

n is 1 to 4; and

Φ, B and Ω are as defined above.

Particularly preferred polypeptides according to the invention (also quoted as combo peptides) are:

```
                        (Combo 1 peptide SEQ ID NO: 1)
FPIPLPYLWLLRALIKRIQALIPKGGRLLPQLVLRLVLRLSGSGSGSGS
IPSSPVHLKRLKLLLLLLLLLILLLILGALLLGL
```

```
                        (Combo 2 peptide SEQ ID NO: 2)
LWLCRALIKRIQALIPKGGRLLPQLVCRLVLRLSGSGIPSSPVHLKRLK
LLLLLLLLLILLLILGALLLGL
```

```
                        (Combo 3 peptide SEQ ID NO: 3)
LWLLRALIKRIQALIPKGGRLLPQLVLRLVLRLSGSGIPSSPVHLKRLK
LLLLLLLLLILLLILGALLLGL
```

-continued (Combo 4 peptide SEQ ID NO: 4)
LWLLRALIRRIQALIPRGGRLLPQLVLRLVLRLSGSGIPSSPVHLRRLR
LLLLLLLLILLLILGALLLGL (Combo peptide SEQ ID NO: 5)
LWLCRALIRRIQALIPRGGRLLPQLVCRLVLRLSGSGIPSSPVHLRRLR
LLLLLLLLILLLILGALLLGL The invention is also directed to nucleic acid sequences encoding for the polypeptides of general formula (I).

An important and well-known feature of the genetic code is its redundancy. That is, for most of the amino acids used to make polypeptides or proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms.

The polypeptides of general formula (I) may be prepared according to synthetic methods well known to the person skilled in the art.

An excellent summary of the many techniques available may be found in J. Meienhofer, Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

The polypeptides of the invention could also be prepared using the solid-phase synthetic technique initially described by Merrifield, in J. Am. Chem. Soc. 85: 2149-2154 (1963). Other polypeptide synthesis techniques may be found, for example, in M. Bodanszky et al., Peptide Synthesis, John Wiley & Sons, 2d Ed., (1976) as well as in other reference works known to those skilled in the art.

Appropriate protective groups for use in such syntheses will be found in the above texts as well as in J. F. W. McOmie, Protective Groups in Organic Chemistry, Plenum Press, New York, NY (1973).

Alternatively, the polypeptides of the invention may be prepared according to recombinant techniques.

In fact, as reported above, it is known that the amino acid residue sequence of a polypeptide is directly related via the genetic code to the deoxyribonucleic acid (DNA) sequence of the structural gene that codes for said polypeptide.

Accordingly, the polypeptides of general formula (I) may be prepared according to recombinant production methods for proteins and peptides, for instance disclosed in Ferrer-Miralles N et al, General introduction: recombinant protein production and purification of insoluble proteins. Methods Mol Biol. 2015; 1258:1-24. In particular, they could be produced recombinantly in *E. coli* or in other host cells known in the art.

Advantageously, the desired peptides are expressed in fusion with a solubility enhancing protein domain that supports correct folding and promotes solubility to its fusion partner, see for instance Esposito, D. & Chatterjee, D. K. Enhancement of soluble protein expression through the use of fusion tags. Curr. Opin. Biotechnol. 17, 353-358 (2006).

Therefore, the present invention is also directed to a process of producing the combo peptides of the invention comprising the following steps:
    a) expressing in a suitable host a fusion protein comprising the combo peptide of the invention with a solubility enhancing tag;
    b) obtaining a mixture containing the fusion protein;

c) optionally isolating the fusion protein;
    d) cleaving the fusion protein to release the desired combo peptide from the residual solubility-enhancing tag or fragments thereof as cleavage products; and
    e) isolating the desired combo peptide.

Preferably, an N-terminal domain (NT) from a spider silk protein (spidroin) could be used as a solubility tag, for example according to the teaching of WO 2017/081239.

The step c) of isolating the fusion protein could be carried according to methods known to the skilled person in the art and could comprise the following steps: c1) precipitation of the fusion protein; and c2) suspending the precipitated fusion protein in an aqueous solvent, wherein the fusion protein is soluble in the aqueous solvent.

Typically, the step e) of isolating the combo peptide of the invention is comprising the step of: e1) extracting the desired combo peptide by suspending the cleavage products in an organic solvent; wherein the desired combo peptide is soluble in the organic solvent; and whereas the residual solubility-enhancing tag or fragments thereof is/are not soluble; e2) filtering and drying the combo peptide according to methods known in the art.

Advantageously, the organic solvent of step e1) is selected from lower alkyl alcohols, such as methanol, ethanol or isopropanol.

The invention further includes the pharmaceutically acceptable salts of the polypeptides of general formula (I) and their blocked N- and/or C-terminus derivatives, e.g via acylation and/or amidation.

Pharmaceutically acceptable salts include for example, salts of hydrochloric acid, acetic acid, and trifluoroacetic acid.

Advantageously, the side-chains and/or the alpha-amino group of the polypeptides might be acylated.

For instance, the serine, cysteine or lysine residues could randomly be linked via ester, thio-ester or amide bonds with one or more saturated or unsaturated acyl groups having from 1 to 24 carbon atoms, preferably from 12 to 18 carbon atoms.

For example, acyl groups could derive from short-chain carboxylic acids such as acetic acid, propionic acid, and butyric acid, and/or from long-chain fatty acids such as lauric acid, myristic, acid, palmitic acid, stearic acid, and oleic acid.

The reconstituted surfactant comprising one or more polypeptides of the invention may be prepared by mixing a solution or a suspension of a polypeptide of general formula (I) and lipids and by subsequently drying the mixture, otherwise they may be prepared by lyophilization or spray-drying.

The proportion of the polypeptides of general formula (I) relative to the reconstituted surfactant can vary and the skilled person in the art shall properly adjust its amount based on the type and/or severity of the disease.

Advantageously each polypeptide may be present in an amount comprised between 0.1 and 10% based on the weight of the surfactant (w/w), preferably between 0.2 and 5%, most preferably between 0.3 and 3%. In some embodiments, the amount may be 0.75% w/w, while in other embodiments it might be 1.5% w/w.

Advantageously, the lipid carrier may comprise the phospholipids that are contained in natural pulmonary surfactant preparations, for example phosphatidylcholines (PC) such as dipalmitoylphosphatidylcholine (DPPC) and palmitoyloleoylphosphatidylcholine (POPC), and phosphatidylglycerols (PG), such as palmitoyloleoylphosphatidylglycerol (POPG) and dipalmitoylphosphatidylglycerol (DPPG).

Other phospholipids which could be advantageously used are phosphatidylinositols (PI), phosphatidylethanolamines (PE), phosphatidylserines and sphingomyelins (SM).

In a particular embodiment, the lipid carrier may comprise further components, for example neutral lipids such as triacylglycerols, free fatty acids and/or cholesterol.

In a particular embodiment the lipid carrier only consists of phospholipids more preferably of a mixture of DPPC and a palmitoyloleylphospholipid selected from POPG or a mixture thereof with POPC in weight ratios ranging from 95:5 to 20:80, preferably from 70:30 to 30:70.

The weight ratio between DPPC and POPG ranges preferably from 75:25 to 65:35, and is more preferably 50:50.

In the case of DPPC:POPG:POPC mixtures, the phospholipids are preferably used in weight ratios of 60:20:20 or 68:16:16, or more preferably in the ratio 50:10:40.

In another embodiment, the lipid carrier may consist of DPPC, DPPG and cholesterol.

In further embodiments, the lipid carrier may consist of one of the mixtures disclosed in WO 2004/105726 or in WO 2014/079898. Otherwise it may comprise the phospholipase-resistant phospho-glycerol derivatives disclosed in WO 2008/011559.

In a particular embodiment of the invention, the reconstituted surfactant comprises as lipid carrier from 0.5 to 2% by weight of one the polypeptides of general formula (I), and a mixture of DPPC and POPG in a weight ratio of 50:50.

In another embodiment, when it is envisaged for use for the treatment of ARDS, the reconstituted surfactant may comprise from 0.3 to 5% by weight of one the polypeptides of general formula (I), and a mixture of DPPC/egg-yolk PC/POPG, in a weight ratio of 50:40:10.

Advantageously the reconstituted surfactant according to the invention essentially comprise from 90 to 99.9% by weight of a lipid carrier, preferably from 95 to 99.5%, more preferably from 97 to 99.25%, the remaining part being the polypeptide.

The present invention also concerns pharmaceutical compositions comprising the reconstituted surfactant of the invention. Said compositions are advantageously administered in the form of a solution, dispersion, suspension or dry powder.

Preferably, said compositions comprise the reconstituted surfactant dissolved or suspended in a suitable solvent or resuspension medium.

More preferably said pharmaceutical compositions are supplied as suspension in a buffered physiological saline aqueous solution in single-use glass vials. Advantageously the reconstituted surfactant concentration (expressed as phospholipid content) is in the range of from about 2 to about 160 mg of surfactant per ml, preferably between 10 and 100 mg/ml, more preferably between 20 and 80 mg/ml.

Said compositions may further comprise electrolytes, such as calcium, magnesium and/or sodium salts, buffers to regulate the pH, and other suitable excipients.

They may also comprise other active ingredients belonging to the classes of steroidal anti-inflammatory agents such as budesonide and beclometasone dipropionate and antibiotics such as tobramycin, and colistin.

The pharmaceutical compositions according to the invention are suitable for the prophylaxis and/or treatment of any disease due to the lack and/or dysfunction of endogenous pulmonary surfactant including, but not limited to, respiratory distress syndrome (RDS) affecting premature neonates (known as nRDS), or paediatric or adult patients (known as ARDS), meconium aspiration syndrome (MAS), and bronchopulmonary dysplasia (BPD).

ARDS could be caused by any direct or indirect lung injury, for instance by pulmonary contusion, inhalation of toxic gases, drowning, sepsis, acute pancreatitis, burns, drug overdose, multiple blood transfusions, or other known causes.

They may also be useful for the prophylaxis and/or treatment of other respiratory disorders such as pneumonia, bronchitis, COPD (chronic obstructive pulmonary disease), and pulmonary condition characterized by excessive mucus secretion or impaired mucus clearance, such as cystic fibrosis, bronchiectasis, primary or secondary ciliary diskinesia as well as for the treatment of serous otitis media (glue ear).

When the patient to be treated is a premature neonate, it can be characterized by either the complete absence of endogenous surfactant or an ineffective amount of endogenous surfactant or an acquired dysfunction of endogenous surfactant during the clinical course.

In either case, the reconstituted surfactant formulation comprising the polypeptides of the invention can be administered in a manner effective to prevent onset of neonatal respiratory distress syndrome (when administered immediately following intubation) or reduce the severity of respiratory deficit in acute respiratory distress syndrome, when administered sometime after initial intubation. The administration of the reconstituted surfactant of the invention may be carried out in a manner known to the person skilled in the art, usually by intratracheal installation (infusion or bolus) using a standard endotracheal tube or, if the patient spontaneously breaths and is kept under non-invasive ventilation, using a catheter for minimally invasive administration, for example according to procedure disclosed in WO 2008/148469 or in Dargaville P A et al Arch Dis Fetal Neonatal Ed 2013, 98(2), 122-126.

Said administration could also occur via aspiration, airway instillation, or through lesser invasive route of administration such as aerosolization, or nebulization.

Administration of the surfactant can be administered periodically over a course of treatment to maintain lung function in the neonate, preferably until the neonate's lung tissue can produce enough endogenous surfactant to maintain lung function in the absence of intervention.

Neonates could be kept under mechanical ventilation or under non-invasive ventilation depending on the severity of the disease.

The subject to be treated can also be a pediatric or adult patient, that otherwise should be able to produce active endogenous surfactant, but due to lung tissue disease or disorder either has deficient levels of endogenous surfactant or existing endogenous surfactant has become inhibited or inactivated in activity.

The following example illustrates the invention in more detail.

EXAMPLES

Example 1—Preparation of the Combo Peptides of the Invention

The Combo peptides SEQ ID NOS: 1 to 5 were expressed as fusion proteins with N-terminal hexaHis-tag and solubility tag (flagelliform spidroin NT variant (FlSpNT*) from Nephila clavipes, Abelein et al, to be published). The genes coding for the fusion proteins (His$_6$-FlSpNT*-Met-Combo peptides 1-5) were ligated into pT7 vectors and transformed into competent *Escherichia coli* BL21(DE3) pLysS cells. The fusion proteins were expressed at 20° C. for 17 h after induction at OD≈0.9 with 0.3 mM isopropyl-β-D-thiogalactopyranoside (IPTG). The cells were then collected by centrifugation and resuspended in 30 ml of 20 mM tris (hydroxymethyl)ammoniummethane-HCl (Tris), pH8, per 1 liter of bacterial culture.

The cells were disrupted by sonication using 85% amplitude, is on, is off for 4 min. After centrifugation at 30000×g for 30 min at 4° C. the soluble fraction was collected and stored at −20° C. The thawed mixture was centrifuged at 25000×g for 30 min at 4° C. and the pellet was collected and re-suspended in 20 mM Tris pH8 by mild sonication (60% amplitude, is on, is off during 3 min). The suspension was incubated overnight in 0.1 M HCl and 50 mM of cyanogen bromide (CNBr) at room temperature to cleave off the His$_6$ and solubility tag and the target Combo peptides were precipitated by centrifugation at 16000×g for 30 min. The pellet was air-dried and weighted. Thereafter each 10 mg of pellet were dissolved in 0.8 ml MeOH and 0.2 ml of 1M KOH and after incubation at 40° C. for 60 min, the alkaline-treated samples were mixed with 1.6 ml CHCl$_3$ and 0.4 ml H$_2$O, thereby creating a two-phase system. The mixture was centrifuged at 2000×g for 5 min, the upper polar phase was discarded and 1 ml MeOH/0.2M KOH (1:1, vol/vol) was added to perform another two-phase separation and this procedure was repeated two times. After centrifugation at 2000×g for 5 min and discarding the upper phase, the lower organic phase was collected and mixed with MeOH. A small amount of 12 M HCl was added to the sample to reduce the pH below 2. Then, the solvent mixture was gently evaporated under reduced pressure, and the product was resuspended in chloroform/methanol, 1:1 (vol/vol), and centrifuged 15 min at 3500×g. The supernatant was collected and evaporated under reduced pressure and the dried sample was resuspended in methanol/ethylene chloride/0.1 M HCl, 85:10:5 (by vol). The peptides were isolated by two consecutive Lipidex-5000 chromatography steps. The solvent system of both columns was methanol/ethylene chloride/0.1 HCl, 85:10:5. The first column was 8×2.5 cm and the second column was 45×1 cm. The dry weight of eluted fractions of both columns was calculated and after the second column chromatography, fractions containing Combo peptides were identified by SDS-PAGE, pooled and used to prepare the synthetic surfactant mixtures. These fractions were also further analyzed by Sephadex LH 60 chromatography, reversed phase (RP)-HPLC and mass spectrometry.

Sephadex LH 60. A Sephadex LH 60 column of 45×1 cm was equilibrated with chloroform/methanol/0.1 HCl, 95:95:10 and the sample was loaded using the same solvent. The fractions eluting were analyzed by SDS-PAGE and their dry weight was calculated.

RP-HPLC. RP-HPLC was performed using a Kromasil 100-5C18 250×4.6 mm column (AkzoNobel, Amsterdam, Netherlands) and an AKTA pure chromatography system (GE Healthcare, Chicago, Illinois, USA). The mobile phase was based on the solvent systems A (40% aqueous ethanol containing 0.1% TFA) and B (isopropanol/0.1% TFA). The column was equilibrated with solvent A and after injection of the sample diluted in solvent A, the peptides were eluted with a linear gradient of solvent B. The eluted peptide was analyzed by SDS-PAGE and mass spectrometry.

Mass spectrometry. Samples were directly infused into a Waters LCT ToF mass spectrometer equipped with an off-line nanospray source (MS Vision) using coated borosilicate capillaries (Thermo). We found that addition of formic acid to a final concentration of 5% greatly increased spectral quality. The capillary voltage was 1.5 kV, the source temperature 80° C., and the cone voltage 200 V. The source pressure was maintained at 0.4 mbar. Spectra were acquired between 500 and 5000 m/z and analyzed using MassLynx 4.1 software (Waters).

Example 2—Preparation of the Synthetic Surfactants

Synthetic surfactant preparations containing 0% (phospholipid only controls), 0.75%, 1.5% 2% or 3% (w/w) of Combo peptides in DPPC/POPG (Sigma-Aldrich, St. Louis, Missouri, USA), 50:50 (by weight) or DPPC/Egg yolk-PC/POPG, 50:40:10 (by weight) were prepared by mixing the phospholipids and the respective peptide in chloroform/methanol 2:1 (v/v), gently evaporating the solvents under reduced pressure and finally resuspending the Combo peptide/phospholipid mixtures in physiological saline at 80 mg/ml of phospholipids.

Example 3—Animal Experiments

New Zealand white rabbits at 27 gestational days (term 31 days) were delivered by caesarian section and anaesthetized at birth with 2 µl/g body weight of Ketaminol® (50 mg/ml)/Domitor® (1 mg/ml)/physiological saline 4:1:15 (by volume). After tracheostomy, the animals received 2.5 ml/kg body weight of poractant alfa, one of the synthetic Combo surfactants, phospholipids only, or no treatment. The animals were placed in small plethysmograph chambers, connected to a ventilator and ventilated without PEEP, with 21% oxygen, at a frequency of 40 breaths/min and an inspiration/expiration ratio 1:1. After all the animals were placed in the ventilator, the lungs were opened with a peak inspiratory pressure (PIP) of 35 cm/H$_2$O for 1 min followed by 15 min at 25 cmH$_2$O, 5 min at 20cmH$_2$O, 5 min at 15cmH$_2$O and finally 5 min at 25 cmH$_2$O. The animals were then ventilated another 5 min at 25cmH$_2$O with 100% N$_2$. The tidal volumes and the compliances were recorded every 5 min during the ventilation period. At the end of the ventilation the animals were sacrificed, and the lungs were removed and weighted. The lung gas volumes were calculated as described by Scherle W in Mikroskopie 26, 57-60 (1970). The statistical analysis was performed using two-way ANOVA for the tidal volumes and one-way ANOVA for the lung gas volumes.

The combo peptides of Example 1, mixed with phospholipids to produce synthetic surfactant preparations according to Example 2, were tested in a rabbit model of neonatal RDS in the absence of PEEP. We compared the effects on tidal volumes and lung gas volumes of Combo surfactant preparations, phospholipids only, poractant alfa and untreated animals.

First, we observed that instillation of phospholipids only (DPPC/Egg yolk-PC/POPG 50:40:10; FIGS. 1A and 1B, or DPPC/POPG 50:50; FIGS. 2A and 2B) were only slightly more effective than giving no treatment, reinforcing that a peptide component is essential for activity of exogenous surfactant.

Furthermore, in order to find a simple phospholipid composition, we tested the efficacy of Combo peptide SEQ ID NO:1 mixed with three or two phospholipid species (FIGS. 1A and 1i).

We observed no statistically significant difference between the results obtained with 1.5% Combo SEQ ID NO:1 in DPPC/Egg yolk-PC/POPG 50:40:10 and in DPPC/POPG 50:50. This outcome indicates that it is possible to use a simple phospholipid mixture with only two components, which is beneficial from a regulatory point of view.

Therefore, in the following experiments we tested combo peptides SEQ ID NOS:1-5 in DPPC/POPG 50:50, and used 1.5% of each combo peptide (FIGS. 2A and 2B). The surfactants containing 1.5% of combo peptides SEQ ID NOS:1,2 and 4 gave higher lung gas volumes than phospholipids alone (p<0.0001, p<0.0001 and p=0.0048, respectively).

All the surfactants containing 1.5% combo peptides gave comparable tidal volumes of poractant alfa. We observed no differences among the tidal volumes and lung gas volumes obtained with combo peptides with the exception of that the lung gas volumes for combo peptide SEQ ID NO:2, which were higher than for combo peptide SEQ ID NO:3.

Finally, we studied the dose dependency from 0.75% to 3% of each combo peptide in DPPC/POPG 50:50 (FIGS. 3A, 3B, 3C, 4A and 4B).

All the synthetic surfactants gave higher lung gas volumes and tidal volumes than the untreated controls.

We observed a concentration dependency of the effect on lung gas volumes.

Importantly, there was no statistical differences between the lung gas volumes after treatment with pulmonary surfactants containing 3% of any combo peptides and poractant alfa, except for 3% combo peptide SEQ ID NO.4. All the surfactants containing 3% combo peptide, except combo peptide SEQ ID NO.4, gave lung gas volumes equal or higher than 11 ml/kg. On the other hand, we recognized a trend where surfactants containing higher Combo peptide concentrations gave lower tidal volumes, but they were still higher than the tidal volumes for poractant alfa.

The lung gas volumes correlated with the macroscopic appearances of the lungs, where higher lung gas volumes correspond to white and pink areas and lower lung gas volumes correspond to brown, liver-like looking lungs.

To sum up, synthetic surfactants made from the combo peptides of the invention are equally active as most used natural derived surfactant for RDS and can be produced in a cost-efficient manner.

---

The invention claimed is:

1. A polypeptide represented by the general formula (I):

```
                                        (SEQ ID NO: 7)
F_qP_qI_qP_qL_qP_qY_qLWLΦZALIZZIQAΩIPZGGZΩLPQLVΦZLVLZLS
(GS)_nG_rIPSSPVHLZZXBXXXXXXXXXXXXXXXXGALLΩ_pG_pL_p (I),
``` wherein:

Ω is an amino acid residue independently selected from the group consisting of M, M oxidized on the sulfur atom, I, L and Nle;

Φ is an amino acid residue independently selected from the group consisting of L, I, and C;

X is an amino acid residue independently selected from the group consisting of I, L, and Nle;

B is an amino acid residue independently selected from the group consisting of K, R, H, W, F, Y, and Orn;

Z is an amino acid independently selected from K or R;

each p and q is independently 0 or 1;

n is an integer between 1 and 8; and r is 0 or 1.

2. The polypeptide according to claim 1, wherein p is 1.

3. The polypeptide according to claim 1, wherein Φ is L.

4. The polypeptide according to claim 1, wherein each X is independently I or L.

5. The polypeptide according to claim 1, wherein n is an integer between 1 and 4.

6. The polypeptide according to claim 1, wherein the polypeptide is represented by the general formula (II):

```
                                        (SEQ ID NO: 8)
FPIPLPYLWLΦZALIZZIQAΩIPZGGZΩLPQLVΦZLVLZLS(GS)_nG_rI
PSSPVHLZZXBXXXXXXXXXXXXXXXXGALLΩ_pG_pL_p (II),
``` and wherein:

n is an integer between 1 and 4; and p, r, Φ, X, B, Ω and Z are as defined in claim 1.

7. The polypeptide according to claim 6, wherein the polypeptide is represented by the general formula (IIa):

```
                                        (SEQ ID NO: 9)
FPIPLPYLWLΦRALIKRIQAΩIPKGGRΩLPQLVΦRLVLRLSGSGSGSGS
IPSSPVHLKRXBXXXXXXXXXXXXXXXXGALLΩGL (IIa),
``` and wherein Φ, X, B and Ω are as defined in claim 1.

8. The polypeptide according to claim 1, wherein the polypeptide is represented by the general formula (IIb):

```
                                        (SEQ ID NO: 10)
FPIPLPYLWLΦRALIKRIQAΩIPKGGRΩLPQLVΦRLVLRLSGSGIPSSP
VHLKRXBXXXXXXXXXXXXXXXXGALLΩGL (IIb),
``` and wherein Φ, X, B and Ω are as defined in claim 1.

9. The polypeptide according to claim 1, wherein the polypeptide is represented by the general formula (IIc):

```
                                        (SEQ ID NO: 11)
FPIPLPYLWLΦRALIKRIQAQIPKGGRΩLPQLVΦRLVLRLSGSGSGSGS
IPSSPVHLKRXBXXXXXXXXXXXXXXXXGALL (IIc),
``` and wherein Φ, X, B and Ω are as defined in claim 1.

10. The polypeptide according to claim 1, wherein the polypeptide is represented by the general formula (IId):

```
                                        (SEQ ID NO: 12)
FPIPLPYLWLΦRALIKRIQAΩIPKGGRΩLPQLVΦRLVLRLSGSGIPSSP
VHLKRXBXXXXXXXXXXXXXXXXGALL (IId),
``` and wherein Φ, X, B and Ω are as defined in claim 1.

11. The polypeptide according to claim 1, wherein the polypeptide is represented by the general formula (III):

```
(SEQ ID NO: 13)
LWLΦRALIKRIQΩAIPKGGRΩLPQLVΦRLVLRLS(GS)_nG_rIPSSPVHL
KRXBXXXXXXXXXXXXXXXXGALLΩpGpLp (III),
``` and wherein:

n is an integer between 1 and 4; and p, r, Φ, X, B and Ω are as defined in claim 1.

12. The polypeptide according to claim 11, wherein the polypeptide is represented by the general formula (IIIe):

```
                                        (SEQ ID NO: 14)
LWLΦRALIKRIQAΩIPKGGRΩLPQLVΦRLVLRLSGSGSGSGSIPSSPVH
LKRXBXXXXXXXXXXXXXXXXGALLΩGL (IIIe),
``` and wherein Φ, X, B and Ω are as defined in claim 11.

13. The polypeptide according to claim 11, wherein the polypeptide is represented by the general formula (IIIf):

```
                                        (SEQ ID NO: 15)
LWLΦRALIKRIQAΩIPKGGRΩLPQLVΦRLVLRLSGSGIPSSPVHLKRXB
XXXXXXXXXXXXXXXXGALLΩGL (IIIf),
``` and wherein Φ, X, B and Ω are as defined in claim 11.

14. The polypeptide according to claim 11, wherein the polypeptide is represented by the general formula (IIIg):

```
                                        (SEQ ID NO: 16)
LWLΦRALIKRIQAΩIPKGGRΩLPQLVΦRLVLRLSGSGSGSGSIPSSPVH
LKRXBXXXXXXXXXXXXXXXXGALL (IIIg),
``` and wherein Φ, X, B and Ω are as defined in claim 11.

15. The polypeptide according to claim 11, wherein the polypeptide is represented by the general formula (IIIh):

```
                                        (SEQ ID NO: 17)
LWLΦRALIKRIQAΩIPKGGRΩLPQLVΦRLVLRLSGSGIPSSPVHLKRXB
XXXXXXXXXXXXXXXXGALL (IIIh),
``` and wherein Φ, X, B and Ω are as defined in claim 11.

16. The polypeptide according to claim 1, wherein the polypeptide is represented by the general formula (IV):

$$
\text{(SEQ ID NO: 18)}
$$
$$
\text{F}_q\text{P}_q\text{I}_q\text{P}_q\text{L}_q\text{P}_q\text{Y}_q\text{LWL}\Phi\text{RALIKRIQA}\Omega\text{IPKGGR}\Omega\text{LPQLV}\Phi\text{RLVLRLS}
$$
$$
\text{(GS)}_n\text{G}_r\text{IPSSPVHLKRXBLLLLLLLLILLLILGALL}\Omega\text{GL (IV),}
$$

and wherein:

n is an integer between 1 and 4; and q, r, $\Phi$, X, B and $\Omega$ are as defined in claim 1.

17. The polypeptide according to claim 16 wherein the polypeptide is represented by the general formula (IVi):

$$
\text{(SEQ ID NO: 19)}
$$
$$
\text{FPIPLPYLWL}\Phi\text{RALIKRIQA}\Omega\text{IPKGGR}\Omega\text{LPQLV}\Phi\text{RLVLRLS(GS)}_n\text{G}_r\text{I}
$$
$$
\text{PSSPVHLKRXBLLLLLLLLILLLILGALL}\Omega\text{GL (IVi),}
$$

and wherein n, r, $\Phi$, X, B and $\Omega$ are as defined in claim 16.

18. The polypeptide according to claim 1, wherein the polypeptide is represented by the general formula (IVl):

$$
\text{(SEQ ID NO: 20)}
$$
$$
\text{LWL}\Phi\text{RALIKRIQA}\Omega\text{IPKGGR}\Omega\text{LPQLV}\Phi\text{RLVLRLS(GS)}_n\text{G}_r\text{IPSSPVHL}
$$
$$
\text{KRXBLLLLLLLLILLLILGALL}\Omega\text{GL (IVl),}
$$

and wherein:

n is an integer between 1 and 4; and r, $\Phi$, X, B and $\Omega$ are as defined in claim 1.

19. The polypeptide according to claim 1, wherein the polypeptide is selected from the group consisting of:

$$
\text{(SEQ ID NO: 1)}
$$
$$
\text{FPIPLPYLWLLRALIKRIQALIPKGGRLLPQLVLRLVLRLSGSGSGSGS}
$$
$$
\text{IPSSPVHLKRLKLLLLLLLLILLLLILGALLLGL,}
$$

$$
\text{(SEQ ID NO: 2)}
$$
$$
\text{LWLCRALIKRIQALIPKGGRLLPQLVCRLVLRLSGSGIPSSPVHLKRLK}
$$
$$
\text{LLLLLLLLILLLILGALLLGL,}
$$

$$
\text{(SEQ ID NO: 3)}
$$
$$
\text{LWLLRALIKRIQALIPKGGRLLPQLVLRLVLRLSGSGIPSSPVHLKRLK}
$$
$$
\text{LLLLLLLLILLLILGALLLGL,}
$$

$$
\text{(SEQ ID NO: 4)}
$$
$$
\text{LWLLRALIRRIQALIPRGGRLLPQLVLRLVLRLSGSGIPSSPVHLRRLR}
$$
$$
\text{LLLLLLLLILLLILGALLLGL, and}
$$

-continued $$
\text{(SEQ ID NO: 5)}
$$
$$
\text{LWLCRALIRRIQALIPRGGRLLPQLVCRLVLRLSGSGIPSSPVHLRRLR}
$$
$$
\text{LLLLLLLLILLLILGALLLGL.}
$$

20. A reconstituted surfactant comprising one or more polypeptides according to claim 1 in admixture with a lipid carrier.

21. The reconstituted surfactant according to claim 20, wherein the lipid carrier comprises a mixture of phospholipids.

22. The reconstituted surfactant according to claim 21, wherein the mixture of phospholipids comprises:

dipalmitoyl phosphatidylcholine (DPPC), and a palmitoyl oleoyl phospholipid selected from (i) palmitoyl oleoyl phosphatidylglycerol (POPG) or (ii) a mixture of POPG with palmitoyl oleoyl phosphatidylcholine (POPC) in a ratio ranging from 95:5 to 20:80 by weight.

23. The reconstituted surfactant according to claim 22, wherein the mixture of phospholipids consists of DPPC:egg-yolk PC:POPG in a ratio of 50:40:10 by weight.

24. A pharmaceutical composition comprising the reconstituted surfactant according to claim 20.

25. The pharmaceutical composition according to claim 24, wherein the pharmaceutical composition is in the form of solution, dispersion, suspension or dry powder.

26. The pharmaceutical composition according to claim 24, wherein the pharmaceutical composition is in the form of an aqueous suspension.

27. The pharmaceutical composition according to claim 26, wherein the pharmaceutical composition comprises the reconstituted surfactant at a concentration of between 2 mg/ml and 160 mg/ml.

28. The pharmaceutical composition according to claim 27, wherein the concentration of the reconstituted surfactant is between 20 mg/ml and 80 mg/ml.

29. A method for treating a neonatal or acute respiratory distress syndrome (RDS) in a subject in need thereof, wherein the method comprises administering to the subject a therapeutically effective amount of one or more polypeptides according to claim 19.

30. A kit comprising: a) the reconstituted surfactant according to claim 20 in a powder form in a first unit dosage form; b) a pharmaceutically acceptable carrier in a second unit dosage form; and c) containers for containing said first and second dosage forms.

\* \* \* \* \*

SEQUENCE LISTING

```
<160> NUMBER OF SEQ ID NOS: 20

<210> SEQ ID NO 1
<211> LENGTH: 82
<212> TYPE: PRT
<213> ORGANISM: Unknown
<220> FEATURE:
<223> OTHER INFORMATION: Artificial polypeptide

<400> SEQUENCE: 1

Phe Pro Ile Pro Leu Pro Tyr Leu Trp Leu Leu Arg Ala Leu Ile Lys
1               5                   10                  15

Arg Ile Gln Ala Leu Ile Pro Lys Gly Gly Arg Leu Leu Pro Gln Leu
            20                  25                  30

Val Leu Arg Leu Val Leu Arg Leu Ser Gly Ser Gly Ser Gly Ser Gly
        35                  40                  45

Ser Ile Pro Ser Ser Pro Val His Leu Lys Arg Leu Lys Leu Leu Leu
    50                  55                  60

Leu Leu Leu Leu Leu Ile Leu Leu Leu Ile Leu Gly Ala Leu Leu Leu
65                  70                  75                  80

Gly Leu

<210> SEQ ID NO 2
<211> LENGTH: 70
<212> TYPE: PRT
<213> ORGANISM: Unknown
<220> FEATURE:
<223> OTHER INFORMATION: Artificial polypeptide

<400> SEQUENCE: 2

Leu Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Leu Ser Gly Ser Gly Ile Pro Ser Ser Pro Val His Leu Lys Arg Leu
        35                  40                  45

Lys Leu Leu Leu Leu Leu Leu Leu Leu Ile Leu Leu Leu Ile Leu Gly
    50                  55                  60

Ala Leu Leu Leu Gly Leu
65                  70
```

-continued

```
<210> SEQ ID NO 3
<211> LENGTH: 70
<212> TYPE: PRT
<213> ORGANISM: Unknown
<220> FEATURE:
<223> OTHER INFORMATION: Artificial polypeptide

<400> SEQUENCE: 3

Leu Trp Leu Leu Arg Ala Leu Ile Lys Arg Ile Gln Ala Leu Ile Pro
1               5                   10                  15

Lys Gly Gly Arg Leu Leu Pro Gln Leu Val Leu Arg Leu Val Leu Arg
            20                  25                  30

Leu Ser Gly Ser Gly Ile Pro Ser Ser Pro Val His Leu Lys Arg Leu
        35                  40                  45

Lys Leu Leu Leu Leu Leu Leu Leu Ile Leu Leu Leu Ile Leu Gly
    50                  55                  60

Ala Leu Leu Leu Gly Leu
65                  70

<210> SEQ ID NO 4
<211> LENGTH: 70
<212> TYPE: PRT
<213> ORGANISM: Unknown
<220> FEATURE:
<223> OTHER INFORMATION: Artificial polypeptide

<400> SEQUENCE: 4

Leu Trp Leu Leu Arg Ala Leu Ile Arg Arg Ile Gln Ala Leu Ile Pro
1               5                   10                  15

Arg Gly Gly Arg Leu Leu Pro Gln Leu Val Leu Arg Leu Val Leu Arg
            20                  25                  30

Leu Ser Gly Ser Gly Ile Pro Ser Ser Pro Val His Leu Arg Arg Leu
        35                  40                  45

Arg Leu Leu Leu Leu Leu Leu Leu Ile Leu Leu Leu Ile Leu Gly
    50                  55                  60

Ala Leu Leu Leu Gly Leu
65                  70

<210> SEQ ID NO 5
<211> LENGTH: 70
<212> TYPE: PRT
<213> ORGANISM: Unknown
<220> FEATURE:
<223> OTHER INFORMATION: Artificial polypeptide

<400> SEQUENCE: 5

Leu Trp Leu Cys Arg Ala Leu Ile Arg Arg Ile Gln Ala Leu Ile Pro
1               5                   10                  15

Arg Gly Gly Arg Leu Leu Pro Gln Leu Val Cys Arg Leu Val Leu Arg
            20                  25                  30

Leu Ser Gly Ser Gly Ile Pro Ser Ser Pro Val His Leu Arg Arg Leu
        35                  40                  45

Arg Leu Leu Leu Leu Leu Leu Leu Ile Leu Leu Leu Ile Leu Gly
    50                  55                  60

Ala Leu Leu Leu Gly Leu
65                  70

<210> SEQ ID NO 6
<211> LENGTH: 7
<212> TYPE: PRT
```

-continued

```
<213> ORGANISM: Unknown
<220> FEATURE:
<223> OTHER INFORMATION: Artificial peptide

<400> SEQUENCE: 6

Phe Pro Ile Pro Leu Pro Tyr
1               5

<210> SEQ ID NO 7
<211> LENGTH: 76
<212> TYPE: PRT
<213> ORGANISM: Unknown
<220> FEATURE:
<223> OTHER INFORMATION: artificial polypeptide
<220> FEATURE:
<221> NAME/KEY: VARIANT
<222> LOCATION: (1)..(1)
<223> OTHER INFORMATION: optional Phe residue
<220> FEATURE:
<221> NAME/KEY: VARIANT
<222> LOCATION: (2)..(2)
<223> OTHER INFORMATION: optional Pro residue
<220> FEATURE:
<221> NAME/KEY: VARIANT
<222> LOCATION: (3)..(3)
<223> OTHER INFORMATION: optional Ile residue
<220> FEATURE:
<221> NAME/KEY: VARIANT
<222> LOCATION: (4)..(4)
<223> OTHER INFORMATION: optional Pro residue
<220> FEATURE:
<221> NAME/KEY: VARIANT
<222> LOCATION: (5)..(5)
<223> OTHER INFORMATION: optional Leu residue
<220> FEATURE:
<221> NAME/KEY: VARIANT
<222> LOCATION: (6)..(6)
<223> OTHER INFORMATION: optional Pro residue
<220> FEATURE:
<221> NAME/KEY: VARIANT
<222> LOCATION: (7)..(7)
<223> OTHER INFORMATION: optional Tyr residue
<220> FEATURE:
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (12)..(12)
<223> OTHER INFORMATION: residue selected from Lys and Arg
<220> FEATURE:
<221> NAME/KEY: VARIANT
<222> LOCATION: (16)..(16)
<223> OTHER INFORMATION: residue selected from Lys and Arg
<220> FEATURE:
<221> NAME/KEY: VARIANT
<222> LOCATION: (17)..(17)
<223> OTHER INFORMATION: residue selected from Lys and Arg
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (24)..(24)
<223> OTHER INFORMATION: residue selected from Lys and Arg
<220> FEATURE:
<221> NAME/KEY: VARIANT
<222> LOCATION: (27)..(27)
<223> OTHER INFORMATION: residue selected from Lys and Arg
<220> FEATURE:
<221> NAME/KEY: VARIANT
<222> LOCATION: (28)..(28)
<223> OTHER INFORMATION: residue selected from Met, Met oxidized at
      sulfur atom, Ile, Leu and nLeu
<220> FEATURE:
```

-continued

```
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (35)..(35)
<223> OTHER INFORMATION: residue selected from Lys and Arg
<220> FEATURE:
<221> NAME/KEY: VARIANT
<222> LOCATION: (39)..(39)
<223> OTHER INFORMATION: residue selected from Lys and Arg
<220> FEATURE:
<221> NAME/KEY: VARIANT
<222> LOCATION: (42)..(42)
<223> OTHER INFORMATION: (Gly-Ser)n with n ranging from 1 to 8
<220> FEATURE:
<221> NAME/KEY: VARIANT
<222> LOCATION: (43)..(43)
<223> OTHER INFORMATION: optional Gly residue
<220> FEATURE:
<221> NAME/KEY: VARIANT
<222> LOCATION: (52)..(52)
<223> OTHER INFORMATION: residue selected from Lys and Arg
<220> FEATURE:
<221> NAME/KEY: VARIANT
<222> LOCATION: (53)..(53)
<223> OTHER INFORMATION: residue selected from Lys and Arg
<220> FEATURE:
<221> NAME/KEY: VARIANT
<222> LOCATION: (54)..(54)
<223> OTHER INFORMATION: residue selected from Ile, Leu and nLeu
<220> FEATURE:
<221> NAME/KEY: VARIANT
<222> LOCATION: (55)..(55)
<223> OTHER INFORMATION: residue selected from Lys, Arg, His, Trp, Phe,
      Tyr and Orn
<220> FEATURE:
<221> NAME/KEY: VARIANT
<222> LOCATION: (56)..(69)
<223> OTHER INFORMATION: residue selected from Ile, Leu and nLeu
<220> FEATURE:
<221> NAME/KEY: VARIANT
<222> LOCATION: (74)..(74)
<223> OTHER INFORMATION: optional residue selected from Met, Met
      oxidized at sulfur atom, Ile, Leu and nLeu
<220> FEATURE:
<221> NAME/KEY: VARIANT
<222> LOCATION: (75)..(75)
<223> OTHER INFORMATION: optional Gly residue
<220> FEATURE:
<221> NAME/KEY: VARIANT
<222> LOCATION: (76)..(76)
<223> OTHER INFORMATION: optional Leu residue

<400> SEQUENCE: 7

Xaa Xaa Xaa Xaa Xaa Xaa Xaa Leu Trp Leu Xaa Xaa Ala Leu Ile Glx
1               5                   10                  15

Glx Ile Gln Ala Xaa Ile Pro Xaa Gly Gly Xaa Xaa Leu Pro Gln Leu
            20                  25                  30

Val Xaa Xaa Leu Val Leu Xaa Leu Ser Xaa Xaa Ile Pro Ser Ser Pro
        35                  40                  45

Val His Leu Xaa Xaa Xaa Xaa Xaa Xaa Xaa Xaa Xaa Xaa Xaa Xaa Xaa
    50                  55                  60

Xaa Xaa Xaa Xaa Xaa Gly Ala Leu Leu Xaa Xaa Xaa
65                  70                  75

<210> SEQ ID NO 8
<211> LENGTH: 76
<212> TYPE: PRT
<213> ORGANISM: Unknown
<220> FEATURE:
<223> OTHER INFORMATION: artificial polypeptide
<220> FEATURE:
```

-continued

```
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (12)..(12)
<223> OTHER INFORMATION: residue selected from Lys and Arg
<220> FEATURE:
<221> NAME/KEY: VARIANT
<222> LOCATION: (16)..(16)
<223> OTHER INFORMATION: residue selected from Lys and Arg
<220> FEATURE:
<221> NAME/KEY: VARIANT
<222> LOCATION: (17)..(17)
<223> OTHER INFORMATION: residue selected from Lys and Arg
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (24)..(24)
<223> OTHER INFORMATION: residue selected from Lys and Arg
<220> FEATURE:
<221> NAME/KEY: VARIANT
<222> LOCATION: (27)..(27)
<223> OTHER INFORMATION: residue selected from Lys and Arg
<220> FEATURE:
<221> NAME/KEY: VARIANT
<222> LOCATION: (28)..(28)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (35)..(35)
<223> OTHER INFORMATION: residue selected from Lys and Arg
<220> FEATURE:
<221> NAME/KEY: VARIANT
<222> LOCATION: (39)..(39)
<223> OTHER INFORMATION: residue selected from Lys and Arg
<220> FEATURE:
<221> NAME/KEY: VARIANT
<222> LOCATION: (42)..(42)
<223> OTHER INFORMATION: (Ser-Gly)n with n ranging from 1 to 4
<220> FEATURE:
<221> NAME/KEY: VARIANT
<222> LOCATION: (43)..(43)
<223> OTHER INFORMATION: optional Gly residue
<220> FEATURE:
<221> NAME/KEY: VARIANT
<222> LOCATION: (52)..(52)
<223> OTHER INFORMATION: residue selected from Lys and Arg
<220> FEATURE:
<221> NAME/KEY: VARIANT
<222> LOCATION: (53)..(53)
<223> OTHER INFORMATION: residue selected from Lys and Arg
<220> FEATURE:
<221> NAME/KEY: VARIANT
<222> LOCATION: (54)..(54)
<223> OTHER INFORMATION: residue selected from Ile, Leu and nLeu
<220> FEATURE:
<221> NAME/KEY: VARIANT
<222> LOCATION: (55)..(55)
<223> OTHER INFORMATION: residue selected from Lys, Arg, His, Trp, Phe,
      Tyr and Orn
<220> FEATURE:
<221> NAME/KEY: VARIANT
<222> LOCATION: (56)..(69)
<223> OTHER INFORMATION: residue selected from Ile, Leu and nLeu
<220> FEATURE:
<221> NAME/KEY: VARIANT
<222> LOCATION: (74)..(74)
<223> OTHER INFORMATION: optional residue selected from Met, Met
      oxidized at sulfur atom, Ile, Leu and nLeu
```

-continued

```
<220> FEATURE:
<221> NAME/KEY: VARIANT
<222> LOCATION: (75)..(75)
<223> OTHER INFORMATION: optional Gly residue
<220> FEATURE:
<221> NAME/KEY: VARIANT
<222> LOCATION: (76)..(76)
<223> OTHER INFORMATION: optional Leu residue

<400> SEQUENCE: 8

Phe Pro Ile Pro Leu Pro Tyr Leu Trp Leu Xaa Xaa Ala Leu Ile Xaa
1               5                   10                  15

Xaa Ile Gln Ala Xaa Ile Pro Xaa Gly Gly Xaa Xaa Leu Pro Gln Leu
            20                  25                  30

Val Xaa Xaa Leu Val Leu Xaa Leu Ser Xaa Xaa Ile Pro Ser Ser Pro
        35                  40                  45

Val His Leu Xaa Xaa Xaa Xaa Xaa Xaa Xaa Xaa Xaa Xaa Xaa Xaa Xaa
    50                  55                  60

Xaa Xaa Xaa Xaa Xaa Gly Ala Leu Leu Xaa Xaa Xaa
65                  70                  75

<210> SEQ ID NO 9
<211> LENGTH: 82
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (28)..(28)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (60)..(60)
<223> OTHER INFORMATION: residue selected from Ile, Leu and nLeu
<220> FEATURE:
<221> NAME/KEY: VARIANT
<222> LOCATION: (61)..(61)
<223> OTHER INFORMATION: residue selected from Lys, Arg, His, Trp, Phe,
      Tyr and Orn
<220> FEATURE:
<221> NAME/KEY: VARIANT
<222> LOCATION: (62)..(75)
<223> OTHER INFORMATION: residue selected from Ile, Leu and nLeu
<220> FEATURE:
<221> NAME/KEY: VARIANT
<222> LOCATION: (80)..(80)
<223> OTHER INFORMATION: residue selected from Met, Met oxidized at
      sulfur atom, Ile, Leu and nLeu

<400> SEQUENCE: 9

Phe Pro Ile Pro Leu Pro Tyr Leu Trp Leu Xaa Arg Ala Leu Ile Lys
1               5                   10                  15

Arg Ile Gln Ala Xaa Ile Pro Lys Gly Gly Arg Xaa Leu Pro Gln Leu
            20                  25                  30

Val Xaa Arg Leu Val Leu Arg Leu Ser Gly Ser Gly Ser Gly Ser Gly
```

```
                35                   40                   45

Ser Ile Pro Ser Ser Pro Val His Leu Lys Arg Xaa Xaa Xaa Xaa Xaa
    50                   55                   60

Xaa Xaa Xaa Xaa Xaa Xaa Xaa Xaa Xaa Xaa Xaa Gly Ala Leu Leu Xaa
65                   70                   75                   80

Gly Leu
```

```
<210> SEQ ID NO 10
<211> LENGTH: 77
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (28)..(28)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (55)..(55)
<223> OTHER INFORMATION: residue selected from Ile, Leu and nLeu
<220> FEATURE:
<221> NAME/KEY: VARIANT
<222> LOCATION: (56)..(56)
<223> OTHER INFORMATION: residue selected from Lys, Arg, His, Trp, Phe,
      Tyr and Orn
<220> FEATURE:
<221> NAME/KEY: VARIANT
<222> LOCATION: (57)..(70)
<223> OTHER INFORMATION: residue selected from Ile, Leu and nLeu
<220> FEATURE:
<221> NAME/KEY: VARIANT
<222> LOCATION: (75)..(75)
<223> OTHER INFORMATION: residue selected from Met, Met oxidized at
      sulfur atom, Ile, Leu and nLeu

<400> SEQUENCE: 10

Phe Pro Ile Pro Leu Pro Tyr Leu Trp Leu Xaa Arg Ala Leu Ile Lys
1                   5                   10                   15

Arg Ile Gln Ala Xaa Ile Pro Lys Gly Gly Arg Xaa Leu Pro Gln Leu
                20                   25                   30

Val Xaa Arg Leu Val Leu Arg Leu Ser Gly Ser Gly Ile Pro Ser Ser
                35                   40                   45

Pro Val His Leu Lys Arg Xaa Xaa Xaa Xaa Xaa Xaa Xaa Xaa Xaa
    50                   55                   60

Xaa Xaa Xaa Xaa Xaa Xaa Gly Ala Leu Leu Xaa Gly Leu
65                   70                   75

<210> SEQ ID NO 11
<211> LENGTH: 79
<212> TYPE: PRT
<213> ORGANISM: Unknown
<220> FEATURE:
<223> OTHER INFORMATION: Artificial polypeptide
<220> FEATURE:
```

-continued

```
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (28)..(28)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (60)..(60)
<223> OTHER INFORMATION: residue selected from Ile, Leu and nLeu
<220> FEATURE:
<221> NAME/KEY: VARIANT
<222> LOCATION: (61)..(61)
<223> OTHER INFORMATION: residue selected from Lys, Arg, His, Trp, Phe,
      Tyr and Orn
<220> FEATURE:
<221> NAME/KEY: VARIANT
<222> LOCATION: (62)..(75)
<223> OTHER INFORMATION: residue selected from Ile, Leu and nLeu

<400> SEQUENCE: 11

Phe Pro Ile Pro Leu Pro Tyr Leu Trp Leu Xaa Arg Ala Leu Ile Lys
1               5                   10                  15

Arg Ile Gln Ala Xaa Ile Pro Lys Gly Gly Arg Xaa Leu Pro Gln Leu
            20                  25                  30

Val Xaa Arg Leu Val Leu Arg Leu Ser Gly Ser Gly Ser Gly Ser Gly
        35                  40                  45

Ser Ile Pro Ser Ser Pro Val His Leu Lys Arg Xaa Xaa Xaa Xaa Xaa
    50                  55                  60

Xaa Xaa Xaa Xaa Xaa Xaa Xaa Xaa Xaa Xaa Xaa Gly Ala Leu Leu
65                  70                  75

<210> SEQ ID NO 12
<211> LENGTH: 74
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (28)..(28)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (55)..(55)
<223> OTHER INFORMATION: residue selected from Ile, Leu and nLeu
<220> FEATURE:
<221> NAME/KEY: VARIANT
```

```
<222> LOCATION: (56)..(56)
<223> OTHER INFORMATION: residue selected from Lys, Arg, His, Trp, Phe,
      Tyr and Orn
<220> FEATURE:
<221> NAME/KEY: VARIANT
<222> LOCATION: (57)..(70)
<223> OTHER INFORMATION: residue selected from Ile, Leu and nLeu

<400> SEQUENCE: 12

Phe Pro Ile Pro Leu Pro Tyr Leu Trp Leu Xaa Arg Ala Leu Ile Lys
1               5                   10                  15

Arg Ile Gln Ala Xaa Ile Pro Lys Gly Gly Arg Xaa Leu Pro Gln Leu
            20                  25                  30

Val Xaa Arg Leu Val Leu Arg Leu Ser Gly Ser Gly Ile Pro Ser Ser
        35                  40                  45

Pro Val His Leu Lys Arg Xaa Xaa Xaa Xaa Xaa Xaa Xaa Xaa Xaa Xaa
    50                  55                  60

Xaa Xaa Xaa Xaa Xaa Xaa Gly Ala Leu Leu
65                  70

<210> SEQ ID NO 13
<211> LENGTH: 69
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (4)..(4)
<223> OTHER INFORMATION: residue selected from Leu, Ile and Cys
<220> FEATURE:
<221> NAME/KEY: VARIANT
<222> LOCATION: (14)..(14)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (27)..(27)
<223> OTHER INFORMATION: residue selected from Leu, Ile and Cys
<220> FEATURE:
<221> NAME/KEY: VARIANT
<222> LOCATION: (35)..(35)
<223> OTHER INFORMATION: (Gly-Ser)n with n ranging from 1 to 4
<220> FEATURE:
<221> NAME/KEY: VARIANT
<222> LOCATION: (36)..(36)
<223> OTHER INFORMATION: optional Gly residue
<220> FEATURE:
<221> NAME/KEY: VARIANT
<222> LOCATION: (47)..(47)
<223> OTHER INFORMATION: residue selected from Ile, Leu and nLeu
<220> FEATURE:
<221> NAME/KEY: VARIANT
<222> LOCATION: (48)..(48)
<223> OTHER INFORMATION: residue selected from Lys, Arg, His, Trp, Phe,
      Tyr and Orn
<220> FEATURE:
<221> NAME/KEY: VARIANT
<222> LOCATION: (49)..(62)
<223> OTHER INFORMATION: residue selected from Ile, Leu and nLeu
<220> FEATURE:
<221> NAME/KEY: VARIANT
<222> LOCATION: (67)..(67)
<223> OTHER INFORMATION: optional residue selected from Met, Met
      oxidized at sulfur atom, Ile, Leu and nLeu
<220> FEATURE:
<221> NAME/KEY: VARIANT
<222> LOCATION: (68)..(68)
```

```
<223> OTHER INFORMATION: optional Gly residue
<220> FEATURE:
<221> NAME/KEY: VARIANT
<222> LOCATION: (69)..(69)
<223> OTHER INFORMATION: optional Leu residue

<400> SEQUENCE: 13

Leu Trp Leu Xaa Arg Ala Leu Ile Lys Arg Ile Gln Ala Xaa Ile Pro
1               5                   10                  15

Lys Gly Gly Arg Xaa Leu Pro Gln Leu Val Xaa Arg Leu Val Leu Arg
            20                  25                  30

Leu Ser Xaa Xaa Ile Pro Ser Ser Pro Val His Leu Lys Arg Xaa Xaa
        35                  40                  45

Xaa Xaa Xaa Xaa Xaa Xaa Xaa Xaa Xaa Xaa Xaa Xaa Xaa Xaa Gly Ala
    50                  55                  60

Leu Leu Xaa Xaa Xaa
65

<210> SEQ ID NO 14
<211> LENGTH: 75
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (4)..(4)
<223> OTHER INFORMATION: residue selected from Leu, Ile and Cys
<220> FEATURE:
<221> NAME/KEY: VARIANT
<222> LOCATION: (14)..(14)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (27)..(27)
<223> OTHER INFORMATION: residue selected from Leu, Ile and Cys
<220> FEATURE:
<221> NAME/KEY: VARIANT
<222> LOCATION: (53)..(53)
<223> OTHER INFORMATION: residue selected from Ile, Leu and nLeu
<220> FEATURE:
<221> NAME/KEY: VARIANT
<222> LOCATION: (54)..(54)
<223> OTHER INFORMATION: residue selected from Lys, Arg, His, Trp, Phe,
      Tyr and Orn
<220> FEATURE:
<221> NAME/KEY: VARIANT
<222> LOCATION: (55)..(68)
<223> OTHER INFORMATION: residue selected from Ile, Leu and nLeu
<220> FEATURE:
<221> NAME/KEY: VARIANT
<222> LOCATION: (73)..(73)
<223> OTHER INFORMATION: residue selected from Met, Met oxidized at
      sulfur atom, Ile, Leu and nLeu

<400> SEQUENCE: 14

Leu Trp Leu Xaa Arg Ala Leu Ile Lys Arg Ile Gln Ala Xaa Ile Pro
1               5                   10                  15

Lys Gly Gly Arg Xaa Leu Pro Gln Leu Val Xaa Arg Leu Val Leu Arg
            20                  25                  30

Leu Ser Gly Ser Gly Ser Gly Ser Gly Ser Ile Pro Ser Ser Pro Val
        35                  40                  45

His Leu Lys Arg Xaa Xaa Xaa Xaa Xaa Xaa Xaa Xaa Xaa Xaa Xaa Xaa
```

```
        50              55              60
Xaa Xaa Xaa Xaa Gly Ala Leu Leu Xaa Gly Leu
65                  70                  75
```

```
<210> SEQ ID NO 15
<211> LENGTH: 70
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (4)..(4)
<223> OTHER INFORMATION: residue selected from Leu, Ile and Cys
<220> FEATURE:
<221> NAME/KEY: VARIANT
<222> LOCATION: (14)..(14)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (27)..(27)
<223> OTHER INFORMATION: residue selected from Leu, Ile and Cys
<220> FEATURE:
<221> NAME/KEY: VARIANT
<222> LOCATION: (48)..(48)
<223> OTHER INFORMATION: residue selected from Ile, Leu and nLeu
<220> FEATURE:
<221> NAME/KEY: VARIANT
<222> LOCATION: (49)..(49)
<223> OTHER INFORMATION: residue selected from Lys, Arg, His, Trp, Phe,
      Tyr and Orn
<220> FEATURE:
<221> NAME/KEY: VARIANT
<222> LOCATION: (50)..(63)
<223> OTHER INFORMATION: residue selected from Ile, Leu and nLeu
<220> FEATURE:
<221> NAME/KEY: VARIANT
<222> LOCATION: (68)..(68)
<223> OTHER INFORMATION: residue selected from Met, Met oxidized at
      sulfur atom, Ile, Leu and nLeu

<400> SEQUENCE: 15

Leu Trp Leu Xaa Arg Ala Leu Ile Lys Arg Ile Gln Ala Xaa Ile Pro
1               5                   10                  15

Lys Gly Gly Arg Xaa Leu Pro Gln Leu Val Xaa Arg Leu Val Leu Arg
                20                  25                  30

Leu Ser Gly Ser Gly Ile Pro Ser Ser Pro Val His Leu Lys Arg Xaa
        35                  40                  45

Xaa Xaa Xaa Xaa Xaa Xaa Xaa Xaa Xaa Xaa Xaa Xaa Xaa Xaa Xaa Gly
    50                  55                  60

Ala Leu Leu Xaa Gly Leu
65                  70
```

```
<210> SEQ ID NO 16
<211> LENGTH: 72
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (4)..(4)
<223> OTHER INFORMATION: residue selected from Leu, Ile and Cys
<220> FEATURE:
<221> NAME/KEY: VARIANT
```

```
<222> LOCATION: (14)..(14)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (27)..(27)
<223> OTHER INFORMATION: residue selected from Leu, Ile and Cys
<220> FEATURE:
<221> NAME/KEY: VARIANT
<222> LOCATION: (53)..(53)
<223> OTHER INFORMATION: residue selected from Ile, Leu and nLeu
<220> FEATURE:
<221> NAME/KEY: VARIANT
<222> LOCATION: (54)..(54)
<223> OTHER INFORMATION: residue selected from Lys, Arg, His, Trp, Phe,
      Tyr and Orn
<220> FEATURE:
<221> NAME/KEY: VARIANT
<222> LOCATION: (55)..(68)
<223> OTHER INFORMATION: residue selected from Ile, Leu and nLeu

<400> SEQUENCE: 16

Leu Trp Leu Xaa Arg Ala Leu Ile Lys Arg Ile Gln Ala Xaa Ile Pro
1               5                   10                  15

Lys Gly Gly Arg Xaa Leu Pro Gln Leu Val Xaa Arg Leu Val Leu Arg
            20                  25                  30

Leu Ser Gly Ser Gly Ser Gly Ser Gly Ser Ile Pro Ser Ser Pro Val
        35                  40                  45

His Leu Lys Arg Xaa Xaa Xaa Xaa Xaa Xaa Xaa Xaa Xaa Xaa Xaa Xaa
    50                  55                  60

Xaa Xaa Xaa Xaa Gly Ala Leu Leu
65                  70

<210> SEQ ID NO 17
<211> LENGTH: 67
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (4)..(4)
<223> OTHER INFORMATION: residue selected from Leu, Ile and Cys
<220> FEATURE:
<221> NAME/KEY: VARIANT
<222> LOCATION: (14)..(14)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (27)..(27)
<223> OTHER INFORMATION: residue selected from Leu, Ile and Cys
<220> FEATURE:
<221> NAME/KEY: VARIANT
<222> LOCATION: (48)..(48)
<223> OTHER INFORMATION: residue selected from Ile, Leu and nLeu
<220> FEATURE:
<221> NAME/KEY: VARIANT
<222> LOCATION: (49)..(49)
<223> OTHER INFORMATION: residue selected from Lys, Arg, His, Trp, Phe,
      Tyr and Orn
<220> FEATURE:
<221> NAME/KEY: VARIANT
```

-continued

```
<222> LOCATION: (50)..(63)
<223> OTHER INFORMATION: residue selected from Ile, Leu and nLeu

<400> SEQUENCE: 17

Leu Trp Leu Xaa Arg Ala Leu Ile Lys Arg Ile Gln Ala Xaa Ile Pro
1               5                   10                  15

Lys Gly Gly Arg Xaa Leu Pro Gln Leu Val Xaa Arg Leu Val Leu Arg
            20                  25                  30

Leu Ser Gly Ser Gly Ile Pro Ser Ser Pro Val His Leu Lys Arg Xaa
        35                  40                  45

Xaa Xaa Xaa Xaa Xaa Xaa Xaa Xaa Xaa Xaa Xaa Xaa Xaa Xaa Xaa Gly
    50                  55                  60

Ala Leu Leu
65

<210> SEQ ID NO 18
<211> LENGTH: 76
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (1)..(1)
<223> OTHER INFORMATION: optional Phe residue
<220> FEATURE:
<221> NAME/KEY: VARIANT
<222> LOCATION: (2)..(2)
<223> OTHER INFORMATION: optional Pro residue
<220> FEATURE:
<221> NAME/KEY: VARIANT
<222> LOCATION: (3)..(3)
<223> OTHER INFORMATION: optional Ile residue
<220> FEATURE:
<221> NAME/KEY: VARIANT
<222> LOCATION: (4)..(4)
<223> OTHER INFORMATION: optional Pro residue
<220> FEATURE:
<221> NAME/KEY: VARIANT
<222> LOCATION: (5)..(5)
<223> OTHER INFORMATION: optional Leu residue
<220> FEATURE:
<221> NAME/KEY: VARIANT
<222> LOCATION: (6)..(6)
<223> OTHER INFORMATION: optional Pro residue
<220> FEATURE:
<221> NAME/KEY: VARIANT
<222> LOCATION: (7)..(7)
<223> OTHER INFORMATION: optional Tyr residue
<220> FEATURE:
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (28)..(28)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (42)..(42)
<223> OTHER INFORMATION: (Gly-Ser)n with n ranging from 1 to 4
<220> FEATURE:
<221> NAME/KEY: VARIANT
```

-continued

```
<222> LOCATION: (43)..(43)
<223> OTHER INFORMATION: optional Gly residue
<220> FEATURE:
<221> NAME/KEY: VARIANT
<222> LOCATION: (54)..(54)
<223> OTHER INFORMATION: residue selected from Ile, Leu and nLeu
<220> FEATURE:
<221> NAME/KEY: VARIANT
<222> LOCATION: (55)..(55)
<223> OTHER INFORMATION: residue selected from Lys, Arg, His, Trp, Phe,
     Tyr and Orn
<220> FEATURE:
<221> NAME/KEY: VARIANT
<222> LOCATION: (74)..(74)
<223> OTHER INFORMATION: residue selected from Met, Met oxidized at
     sulfur atom, Ile, Leu and nLeu

<400> SEQUENCE: 18

Xaa Xaa Xaa Xaa Xaa Xaa Xaa Leu Trp Leu Xaa Arg Ala Leu Ile Lys
1               5                   10                  15

Arg Ile Gln Ala Xaa Ile Pro Lys Gly Gly Arg Xaa Leu Pro Gln Leu
            20                  25                  30

Val Xaa Arg Leu Val Leu Arg Leu Ser Xaa Xaa Ile Pro Ser Ser Pro
        35                  40                  45

Val His Leu Lys Arg Xaa Xaa Leu Leu Leu Leu Leu Leu Leu Leu Ile
    50                  55                  60

Leu Leu Leu Ile Leu Gly Ala Leu Leu Xaa Gly Leu
65                  70                  75

<210> SEQ ID NO 19
<211> LENGTH: 76
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (11)..(11)
<223> OTHER INFORMATION: residue selected from Leu, Ile and Cys
<220> FEATURE:
<221> NAME/KEY: VARIANT
<222> LOCATION: (21)..(21)
<223> OTHER INFORMATION: residue selected from Met, Met oxidized at
     sulfur atom, Ile, Leu and nLeu
<220> FEATURE:
<221> NAME/KEY: VARIANT
<222> LOCATION: (28)..(28)
<223> OTHER INFORMATION: residue selected from Met, Met oxidized at
     sulfur atom, Ile, Leu and nLeu
<220> FEATURE:
<221> NAME/KEY: VARIANT
<222> LOCATION: (34)..(34)
<223> OTHER INFORMATION: residue selected from Leu, Ile and Cys
<220> FEATURE:
<221> NAME/KEY: VARIANT
<222> LOCATION: (42)..(42)
<223> OTHER INFORMATION: (Gly-Ser)n with n ranging from 1 to 4
<220> FEATURE:
<221> NAME/KEY: VARIANT
<222> LOCATION: (43)..(43)
<223> OTHER INFORMATION: optional Gly residue
<220> FEATURE:
<221> NAME/KEY: VARIANT
<222> LOCATION: (54)..(54)
<223> OTHER INFORMATION: residue selected from Ile, Leu and nLeu
<220> FEATURE:
<221> NAME/KEY: VARIANT
<222> LOCATION: (55)..(55)
<223> OTHER INFORMATION: residue selected from Lys, Arg, His, Trp, Phe,
     Tyr and Orn
<220> FEATURE:
<221> NAME/KEY: VARIANT
<222> LOCATION: (74)..(74)
```

-continued

<223> OTHER INFORMATION: residue selected from Met, Met oxidized at
      sulfur atom, Ile, Leu and nLeu

<400> SEQUENCE: 19

Phe Pro Ile Pro Leu Pro Tyr Leu Trp Leu Xaa Arg Ala Leu Ile Lys
1               5                   10                  15

Arg Ile Gln Ala Xaa Ile Pro Lys Gly Gly Arg Xaa Leu Pro Gln Leu
            20                  25                  30

Val Xaa Arg Leu Val Leu Arg Leu Ser Xaa Xaa Ile Pro Ser Ser Pro
        35                  40                  45

Val His Leu Lys Arg Xaa Xaa Leu Leu Leu Leu Leu Leu Leu Leu Ile
    50                  55                  60

Leu Leu Leu Ile Leu Gly Ala Leu Leu Xaa Gly Leu
65                  70                  75

<210> SEQ ID NO 20
<211> LENGTH: 69
<212> TYPE: PRT
<213> ORGANISM: Unknown
<220> FEATURE:
<223> OTHER INFORMATION: Artificial polypeptide
<220> FEATURE:
<221> NAME/KEY: VARIANT
<222> LOCATION: (4)..(4)
<223> OTHER INFORMATION: residue selected from Leu, Ile and Cys
<220> FEATURE:
<221> NAME/KEY: VARIANT
<222> LOCATION: (14)..(14)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (21)..(21)
<223> OTHER INFORMATION: residue selected from Met, Met oxidized at
      sulfur atom, Ile, Leu and nLeu
<220> FEATURE:
<221> NAME/KEY: VARIANT
<222> LOCATION: (27)..(27)
<223> OTHER INFORMATION: residue selected from Leu, Ile and Cys
<220> FEATURE:
<221> NAME/KEY: VARIANT
<222> LOCATION: (35)..(35)
<223> OTHER INFORMATION: (Gly-Ser)n with n ranging from 1 to 4
<220> FEATURE:
<221> NAME/KEY: VARIANT
<222> LOCATION: (36)..(36)
<223> OTHER INFORMATION: optional Gly residue
<220> FEATURE:
<221> NAME/KEY: VARIANT
<222> LOCATION: (47)..(47)
<223> OTHER INFORMATION: residue selected from Ile, Leu and nLeu
<220> FEATURE:
<221> NAME/KEY: VARIANT
<222> LOCATION: (48)..(48)
<223> OTHER INFORMATION: residue selected from Lys, Arg, His, Trp, Phe,
      Tyr and Orn
<220> FEATURE:
<221> NAME/KEY: VARIANT
<222> LOCATION: (67)..(67)
<223> OTHER INFORMATION: residue selected from Met, Met oxidized at
      sulfur atom, Ile, Leu and nLeu

<400> SEQUENCE: 20

Leu Trp Leu Xaa Arg Ala Leu Ile Lys Arg Ile Gln Ala Xaa Ile Pro
1               5                   10                  15

Lys Gly Gly Arg Xaa Leu Pro Gln Leu Val Xaa Arg Leu Val Leu Arg
            20                  25                  30

Leu Ser Xaa Xaa Ile Pro Ser Ser Pro Val His Leu Lys Arg Xaa Xaa
        35                  40                  45

-continued

```
Leu Leu Leu Leu Leu Leu Leu Leu Ile Leu Leu Leu Ile Leu Gly Ala
    50              55              60

Leu Leu Xaa Gly Leu
65
```